US008633197B2

(12) United States Patent
Bongartz et al.

(10) Patent No.: US 8,633,197 B2
(45) Date of Patent: Jan. 21, 2014

(54) PIPERIDINE/PIPERAZINE DERIVATIVES

(75) Inventors: Jean-Pierre André Marc Bongartz, Turnhout (BE); Guy Rosalia Eugeen Van Lommen, Berlaar (BE); Erwin Coesemans, Nijlen (BE); Christophe Francis Robert Nestor Buyck, Hamme (BE)

(73) Assignee: Janssen Pharmaceutica N.V., Beerse (BE)

( * ) Notice: Subject to any disclaimer, the term of this patent is extended or adjusted under 35 U.S.C. 154(b) by 224 days.

(21) Appl. No.: 12/663,007

(22) PCT Filed: Jun. 5, 2008

(86) PCT No.: PCT/EP2008/057011
§ 371 (c)(1),
(2), (4) Date: Dec. 4, 2009

(87) PCT Pub. No.: WO2008/148851
PCT Pub. Date: Dec. 11, 2008

(65) Prior Publication Data
US 2010/0184776 A1 Jul. 22, 2010

(30) Foreign Application Priority Data
Jun. 8, 2007 (EP) .................... 07109864

(51) Int. Cl.
A61K 31/4965 (2006.01)
C07D 241/04 (2006.01)
C07D 295/00 (2006.01)

(52) U.S. Cl.
USPC .................... 514/255.03; 544/392

(58) Field of Classification Search
USPC .................... 514/255.03; 544/392
See application file for complete search history.

(56) References Cited

U.S. PATENT DOCUMENTS

| | | | |
|---|---|---|---|
| 4,698,352 A | 10/1987 | Narita et al. | |
| 5,429,770 A | 7/1995 | Closs et al. | |
| 5,574,055 A | 11/1996 | Borgulya et al. | |
| 5,789,412 A | 8/1998 | Halazy et al. | |
| 6,492,368 B1 | 12/2002 | Dorsch et al. | |
| 6,884,868 B1 | 4/2005 | Tojo et al. | |
| 7,186,683 B2 | 3/2007 | Henriksen et al. | |
| 2003/0055055 A1 | 3/2003 | Teuber et al. | |
| 2003/0060472 A1 | 3/2003 | Learmonth et al. | |
| 2004/0038858 A1 | 2/2004 | Dorsch et al. | |
| 2004/0162282 A1 | 8/2004 | Pennell et al. | |
| 2004/0220191 A1 | 11/2004 | Schwink et al. | |
| 2005/0059650 A1 | 3/2005 | Jones et al. | |
| 2005/0209241 A1 | 9/2005 | Jolidon | |
| 2006/0030612 A1 | 2/2006 | Steffan | |
| 2007/0021339 A1 | 1/2007 | Alloza Miravete et al. | |
| 2007/0207999 A1 | 9/2007 | Stadtmueller et al. | |
| 2007/0249620 A1 | 10/2007 | Kutura et al. | |

FOREIGN PATENT DOCUMENTS

| | | |
|---|---|---|
| CN | 1749256 A | 3/2006 |
| EP | 030371 A | 6/1981 |
| EP | 321131 A | 6/1989 |
| EP | 378207 A | 7/1990 |
| EP | 630954 A | 12/1994 |
| EP | 657440 A | 6/1995 |
| EP | 1764360 A | 3/2007 |
| GB | 1383906 A | 2/1974 |
| JP | 11139969 | 5/1999 |
| JP | 2005/206492 | 8/2005 |
| JP | 2005-330266 A | 12/2005 |
| JP | 2007131584 A | 5/2007 |
| WO | WO 96/01820 A | 1/1996 |
| WO | WO 96/01822 A | 1/1996 |
| WO | 96/21648 A1 | 7/1996 |
| WO | WO 97/05877 A | 2/1997 |
| WO | WO 97/05878 A | 2/1997 |
| WO | 97/30995 A1 | 3/1997 |
| WO | WO 98/24766 A | 6/1998 |
| WO | WO 99/16751 A | 8/1999 |
| WO | 00/05225 | 2/2000 |
| WO | WO 00/32582 A1 | 6/2000 |
| WO | WO 00/71107 | 11/2000 |
| WO | WO 01/58885 A | 8/2001 |
| WO | 01/098251 A1 | 12/2001 |
| WO | WO 01/95856 | * 12/2001 |

(Continued)

OTHER PUBLICATIONS

Abstract, Lee, et al., Inhibition of Diacylglycerol Acyltransferase by Alkamides Isolated from the Fruits of *Piper longum* and *Piper nigrum*, J. Agric. Food Chem., 54, 9759-9763 (2006).*
Chen, et al., Inhibition of Triglyceride Synthesis as a Treatment Strategy for Obesity: Lessons From DGAT1-Deficient Mice, Arteriosclerosis, Thrombosis, and Vascular Biology, 25: 482-486 (2005).*
International Search Report, International Application No. PCT/EP2008/057011, Date of Mailing of International Search Report, Nov. 6, 2008.
Written Opinion of International Search Authority, International Application No. PCT/EP2008/057011.

(Continued)

*Primary Examiner* — Erich A Leeser

(57) ABSTRACT

The invention relates to a DGAT inhibitor of formula (I)

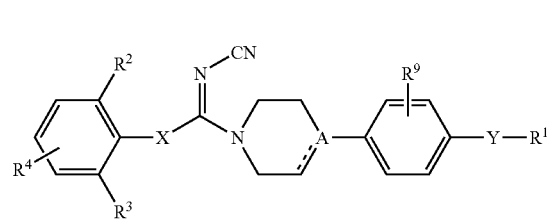

including any stereochemically isomeric form thereof, a N-oxide thereof, a pharmaceutically acceptable salt thereof or a solvate thereof, and methods for preparing such compounds, pharmaceutical compositions comprising said compounds as well as the use as a medicine of said compounds.

13 Claims, No Drawings

(56) References Cited

FOREIGN PATENT DOCUMENTS

| WO | WO 01/97810 A2 | 12/2001 |
|---|---|---|
| WO | WO 02/20501 A2 | 3/2002 |
| WO | WO 02/20501 A3 | 3/2002 |
| WO | 02/48117 A1 | 6/2002 |
| WO | 02/055012 A1 | 7/2002 |
| WO | WO 02/081460 A1 | 10/2002 |
| WO | WO 03/064386 A | 8/2003 |
| WO | 03/076421 A1 | 9/2003 |
| WO | 03/076422 A1 | 9/2003 |
| WO | WO 03/082864 A | 10/2003 |
| WO | 2004/018439 A1 | 3/2004 |
| WO | 2004/047755 A2 | 6/2004 |
| WO | WO 2004/047755 A2 | 6/2004 |
| WO | 2004/069792 | 8/2004 |
| WO | WO 2004/072025 A | 8/2004 |
| WO | 2006/047277 A1 | 10/2004 |
| WO | 2004/100881 A2 | 11/2004 |
| WO | WO 2004/100881 A2 | 11/2004 |
| WO | 2004/110375 A2 | 12/2004 |
| WO | WO 2004/110375 A2 | 12/2004 |
| WO | 2005/072740 A3 | 8/2005 |
| WO | WO 2005/072740 A3 | 8/2005 |
| WO | 2006/004200 A1 | 1/2006 |
| WO | WO 2006/004200 A1 | 1/2006 |
| WO | 2006/034441 A1 | 3/2006 |
| WO | WO 2006/034441 A1 | 3/2006 |
| WO | 2006/038039 A | 4/2006 |
| WO | 2006/038039 A1 | 4/2006 |
| WO | 2006/044775 A | 4/2006 |
| WO | WO 2006/038039 A | 4/2006 |
| WO | WO 2006/044775 A | 4/2006 |
| WO | 2006/064189 | 6/2006 |
| WO | 2006/067071 A1 | 6/2006 |
| WO | WO 2006/067071 A1 | 6/2006 |
| WO | 2006/086445 A3 | 8/2006 |
| WO | WO 2006/086445 A3 | 8/2006 |
| WO | 2006/094842 A | 9/2006 |
| WO | WO 2006/094842 A | 9/2006 |
| WO | 2006/105127 A2 | 10/2006 |
| WO | 2006/106326 A | 10/2006 |
| WO | 2006/113919 A2 | 10/2006 |
| WO | 2006/113919 A3 | 10/2006 |
| WO | WO 2006/106326 A | 10/2006 |
| WO | WO 2006/113919 A2 | 10/2006 |
| WO | WO 2006/113919 A3 | 10/2006 |
| WO | 2006/134317 A | 12/2006 |
| WO | WO 2006/134317 A | 12/2006 |
| WO | 2007/071966 | 6/2007 |
| WO | 2007/096351 | 8/2007 |
| WO | 2007/100990 A | 9/2007 |
| WO | WO 2007/100990 A | 9/2007 |
| WO | 2008/003766 | 1/2008 |
| WO | 2008/122787 A1 | 10/2008 |
| WO | 2008/141976 A1 | 11/2008 |
| WO | WO 2008/141976 A1 | 11/2008 |
| WO | 2008/148840 A1 | 12/2008 |
| WO | 2008/148849 A2 | 12/2008 |
| WO | 2008/148868 A1 | 12/2008 |
| WO | WO 2008/148840 A1 | 12/2008 |
| WO | WO 2008/148849 A2 | 12/2008 |
| WO | WO 2008/148868 A1 | 12/2008 |
| WO | 2009/147170 A2 | 12/2009 |

OTHER PUBLICATIONS

Birch et al., "DGAT1 inhibitors as anti-obesity and anti-diabetic agents.", *Current Opinion in Drug Discovery & Development*, 2010, pp. 489-496, vol. 13(4), Thomas Reuters.

Chen et al., "Enhancing eneryg and glucose metabolism by disruption triglyceride sysnthesis; Lessons from mice lacking DGAT1.", *Nutrition & Metabolism*, Jan. 31, 2006; pp. 1-4, vol. 3(10).

Chen et al., "DGAT and Triglyceride Synthesis: A New Target for Obesity Treatment?", *Trends Cardiovasc. Med.*, 2000, pp. 188-192, vol. 10(5).

Chen et al., "Inhibition of Triglyceride Synthesis as a Treatment Strategy for Obesity. Lessons from DGAT1-Deficient Mice.", *Arterioscler. Thromb. Vasc. Biol.*, 2005, pp. 482-486, vol. 25.

Matsuda and Tomoda, "DGAT inhibitors for obesity", *Current Opinion in Investigational Drugs*, 2007, pp. 836-841, vol. 8(10).

Okawa et al., "Role of MGAT2 and DGAT1 in the release of gut peptides after triglyceride ingestion", *Biochemical and Biophysical Research Communications*, 2009, pp. 377-381, vol. 390.

Cases et al., "Identification of a gene encoding an acyl CoA:diacylglycerol acyltransferase, a key enzyme in triacylglycerol synthesis.", Proc. Natl. Acad. Sci., Oct. 1998, vol. 95, pp. 13018-13023.

Chen et al., "Increased insulin and leptin sensitivity in mice lacking acyl CoA:diacylglycerol acyltransferase 1.", J. Clin. Invest., 2002, vol. 109(8), pp. 1049-1055.

Glass et al., "4-(4-Guanidinobenzoyl)-2-Imidazolones and Related Compounds: Phosphodiesterase Inhibitors and Novel Cardiotonics With Combined Histamine H2 Receptor Agonist and PDE III Inhibitor Activity.", Archiv. Der Pharmazie, 1995, vol. 328 (10), pp. 709-719, XP009002222.

Wu et al., "Synthesis and platelet aggregation inhibitory activities of 6-[4(4-substituted-piperazine-1-yl)phenyl]-5-methyl-4,5-dihydro-3(2H)-pyridazinone derivatives.", Database CA, Chemical Abstracts Service, XP002459096, (2000).

Database Registry, Apr. 17, 2007, XP002458843.

Vippagunta et al., "Crystalline Solids.", Advanced Drug Delivery Reviews, 2001, pp. 3-26, vol. 48.

Kuwabara et al., "A Nove Novel Selective Peroxisome Proliferator-Activated Receptor Agonist, 2-Methyl-c-5-[4-[5-methyl-2-(4-methylphenyl)-4-oxazolyl]butyl]-1,3-dioxane-r-2-carboxylic acid (NS-220), Potently Decreases Plasma Triglyceride and Glucose Levels and Modifies Lipoprotein Profiles in KK-Ay Mice.", J. Pharmacol. Exp. Ther., 2004, pp. 970-977, vol. 309(3).

Bose et al., "Glucagon-like Peptide 1 Can Directly Protect the Heart Against Ischemia/Reperfusion Injury.", Diabetes, Jan. 2005, vol. 54, pp. 146-151.

Buhman et al., "DGAT1 Is Not Essential for Intestinal Triacylglycerol Absorption or Chylomicron Synthesis.", J. Biol. Chem. Jul. 12, 2002, vol. 277(28), pp. 25474-25479.

Cases et al., "Cloning of DGAT2, a Second Mammalian Diacylglycerol Acyltransferase, and Related Family Members.", J. Biol. Chem., Oct. 19, 2001, vol. 276(42), pp. 38870-38876.

Cases et al., "Identification of a gene encoding an acyl CoA: diacylglycerol acyltransferase, a key enzyme in triacylglycerol synthesis.", Proc. Natl. Acad. Sci., Oct. 1998, vol. 95, pp. 13018-13023.

Chen et al., "DGAT and Triglyceride Synthesis: A New Target for Obesity Treatment?", Trends Cardiovasc. Med., 2000, vol. 10(5), pp. 188-192.

Chen et al., "Increased insulin and leptin sensitivity in mice lacking acyl CoA: diacylglycerol acyltransferase 1.", J. Clin. Invest., 2002, vol. 109(8), pp. 1049-1055.

Database Registry, Aug. 3, 2005, XP002501332.
Database Registry, Aug. 5, 2005, XP002501333.
Database Registry, Aug. 8, 2005, XP002501334.
Database Registry, Aug. 8, 2005, XP002501335.
Database Registry, Mar. 22, 2004, XP002459101.
Database Registry, Mar. 22, 2004, XP002459102.
Database Registry, Mar. 22, 2004, XP002459103.
Database Registry, Nov. 3, 2004, XP002459099.

Farese et al., "Triglyceride synthesis: insights from the cloning of diacylglycerol acytransferase.", Curr. Opin. Lipidol. 2000, vol. 11, pp. 229-234.

Glass et al., "4-(4-Guanidinobenzoyl)-2-Imidazolones And Related Compounds: Phosphodiesterase Inhibitors and Novel Cardiotonics With Combined Histamine H2 Receptor Agonist and PDE III Inhibitor Activity.", Archiv. Der Pharmazie, 1995, vol. 328 (10), pp. 709-719, XP009002222.

Griffett et al., "Effects of 6-[p(4-phenylacetylpiperazine-1-yl)phenyl1]-4, 5-dihydro-3(2 H)pyridazinone (CCI 17810) and aspirin on platelet aggregation and adhesiveness.", Database Medline, British J. of Pharmacology, Apr. 1981, vol. 72(4), pp. 697-705, XP002459094.

(56) References Cited

OTHER PUBLICATIONS

Jiang et al., "Synthesis and platelet aggregation inhibitory activity of 6-(4-substituted phenyl)-4,5-dihydro-3(2H)-pyridazinones.", Database CA, Chemical Abstracts Service, XP002459098, (1990).

Khalaj et al., "Synthesis and antibacterial activity of 2-(4-substituted phenyl)-3(2H)-isothiazolones.", European Journal of Med. Chem., Aug. 2004, vol. 39(8), pp. 699-705, Paris, France, XP004523234.

Lewis et al., "Disordered fat storage and mobilization in the pathogenesis of insulin resistance and type 2 diabetes.", Endocrine Reviews, 2002, vol. 23(1), pp. 201-229.

Malloy and Kane, Pathogenesis and treatment in cardiomyopathy., Adv. Intern. Med., 2001, vol. 47, pp. 111-136.

Nikolaidis et al., "Glucagon-Like Peptide-1 Limits Myocardial Stunning following Brief Coronary Occlusion and Reperfusion in Conscious Canines.", Journal of Pharm. and Experimental Therapeutics, 2005, vol. 312(1), pp. 303-308.

Oelkers et al., "Characterizations of Two Human Genes Encoding Acyl Coenzyme A: Cholesterol Acyltransferase-related Enzymes.", J. Biol. Chem., Oct. 8, 1998, vol. 273(41), pp. 26765-26771, U.S.A.

Pearson et al., "Preparation of Functionalized P-Phenylenediamine Derivatives using Arene-Iron Chemistry.", J. of Org. Chem., 1996, vol. 61(4), pp. 1297-1305, Easton, US, XP002938137.

Perry et al., "Evidence of GLP-1-mediated neuroprotection in an animal model of pyridoxine-induced peripheral sensory neuropathy.", Experimental Neurology, 2007, vol. 203(2), pp. 293-301.

Smith et al., "Obesity resistance and multiple mechanisms of triglyceride synthesis in mice lacking DGAT.", Nature Genetics May 2000, vol. 25(1), pp. 87-90.

Stone et al., "Lipopenia and Skin Barrier Abnormalities in DGAT2-deficient Mice.", J. Biol. Chem., Mar. 19, 2004, vol. 279(12), pp. 11767-11776.

Wu et al., "Synthesis and platelet aggregation inhibitory activities of 6-[4(4-substituted-piperazine-1-yl)phenyl]-5-methyl-4,5-dihydro-3(2H)-pyridazinone derivatives.", Database CA, Chemical Abstracts, (2002).

Zhang et al., "Synthesis and platelet aggregation inhibitory activity of pyridazinones.", Database CA, Chemical Abstracts Service, XP002459097, (1994).

Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095, (2002).

Shandala et al., "Reactions of Acetylenic Esters with Cyclic Ketones and Substituted Acetophenones.", Journal f. prakt. Chemic. Band, 1979, pp. 899-904, vol. 321(6).

Aarmadaka et al., "Synthesis and Evaluation of Urea and Thiourea Derivatives of Oxazolidinones as Antibacterial Agents.", Chem. Pharm. Bull., Feb. 1, 2007, ppl 236-240, vol. 55.

Phillips et al., "Structure-antibacterial activity of arylcarbonyl- and arylsulfonyl-piperazine 5-Triazolylmethyl oxazolidinones.", Eur. J. Med. Chem., Nov. 29, 2006, pp. 214-225, vol. 42.

Chinese J. Med. Chem., 1994, pp. 162-170, vol. 4.

Watt, M.J., "Storing Up Trouble: Does Accumulation of Intramyocellular Triglyceride Protect Skeletal Muscle from Insulin Resistance?", Clinical and Experimental Pharmacolgy and Physiology, 2009, pp. 5-11, vol. 36.

Farese et al., "Lipopenia and Skin Barrier Abnormalities in DGAT2-deficient Mice*.", J. Biol. Chem., Mar. 19, 2004, pp. 11767-1176, vol. 279(12).

Abstract RN854989-58-5.
Abstract RN859099-41-5.
Abstract RN859135-44-7.
Abstract RN859646-88-1.
Abstract RN860081-71-6.
Abstract RN860458-98-6.
Abstract RN861994-10-7.
Abstract RN884476-57-7.
Abstract RN892188-37-3.
Abstract RN892208-87-6.
Abstract RN892693-34-4.
Abstract RN897172-00-8.
Abstract RN897548-47-9.
Abstract RN898117-91-4.

\* cited by examiner

PIPERIDINE/PIPERAZINE DERIVATIVES

CROSS REFERENCE TO RELATED APPLICATIONS

This application is the US national stage of Application No. PCT/EP2008/057011, filed Jun. 5, 2008, which application claims priority from EP 07109864.4, filed Jun. 8, 2007.

FIELD OF THE INVENTION

The present invention relates to the use of a DGAT inhibitor, in particular a DGAT1 inhibitor, for the manufacture of a medicament for the prevention or the treatment of a disease by elevating the levels of one or more satiety hormones, in particular GLP-1. The present invention also concerns piperidine/piperazine derivatives having DGAT inhibitory activity, in particular DGAT1 inhibitory activity. The invention further relates to methods for their preparation and pharmaceutical compositions comprising them. The invention also relates to the use of said compounds for the manufacture of a medicament for the prevention or the treatment of a disease mediated by DGAT, in particular DGAT 1.

BACKGROUND TO THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv. Intern. Med.* (2001) 47:11 1).

Additionally, hypertriglyceridemia is often an adverse consequence of cancer therapy (see, Bast, et al. *Cancer Medicine*, 5th Ed., (2000) B. C. Decker, Hamilton, Ontario, Calif.).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol (DAG) and fatty acyl CoA to form triglycerides (TG) at the endoplasmic reticulum (reviewed in Chen and Farese, *Trends Cardiovasc. Med.* (2000) 10: 188 and Farese, et al, *Curr. Opin. Lipidol.* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored. Genes encoding mouse DGAT1 and the related human homologs ARGP1 (human DGAT1) and ARGP2 (human ACAT2) now have been cloned and characterized (Cases, et al, *Pro.c Nat.l Acad. Sci.* (1998) 95:13018; Oelkers, et al, *J. Biol. Chem.* (1998) 273:26765). The gene for mouse DGAT1 has been used to create DGAT knock-out mice to better elucidate the function of the DGAT gene.

Unexpectedly, mice unable to express a functional DGAT1 enzyme (Dgat1−/− mice) are viable and still able to synthesize triglycerides, indicating that multiple catalytic mechanisms contribute to triglyceride synthesis (Smith, et al, Nature Genetics (2000) 25:87). Other enzymes that catalyze triglyceride synthesis, for example, DGAT2 and diacylglycerol transacylase, also have been identified (Cases, et al, *J. Biol. Chem.* (2001) 276:38870). Gene knockout studies in mice have revealed that DGAT2 plays a fundamental role in mammalian triglyceride synthesis and is required for survival. DGAT2 deficient mice are lipopenic and die soon after birth, apparently from profound reductions in substrates for energy metabolism and from impaired permeability barrier function in the skin. (Farese, et al., *J. Biol. Chem.* (2004) 279: 11767).

Significantly, Dgat1−/− mice are resistant to diet-induced obesity and remain lean. Even when fed a high fat diet (21% fat) Dgat1−/− mice maintain weights comparable to mice fed a regular diet (4% fat) and have lower total body triglyceride levels. The obesity resistance in Dgat1−/− mice is not due to decreased caloric intake, but the result of increased energy expenditure and decreased resistance to insulin and leptin (Smith, et al, Nature Genetics (2000) 25:87; Chen and Farese, *Trends Cardiovasc. Med.* (2000) 10: 188; and Chen, et al, *J. Clin. Invest*. (2002) 109:1049). Additionally, Dgat1−/− mice have reduced rates of triglyceride absorption (Buhman, et al, *J. Biol. Chem.* (2002) 277:25474). In addition to improved triglyceride metabolism, Dgat1−/− mice also have improved glucose metabolism, with lower glucose and insulin levels following a glucose load, in comparison to wild-type mice (Chen and Farese, *Trends Cardiovasc. Med*. (2000) 10: 188).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically inhibit the catalytic activity of DGAT, in particular DGAT1.

We have now unexpectedly found that the compounds of the present invention exhibit DGAT inhibitory activity, in particular DGAT1 inhibitory activity, and can therefore be used to prevent or treat a disease associated with or mediated by DGAT, such as for example obesity, type II diabetes, heart disease and cancer. The compounds of the invention differ from the prior art compounds in structure, in their pharmacological activity, pharmacological potency, and/or pharmacological profile.

We have also unexpectedly found that DGAT inhibitors can be used to elevate the levels of one or more satiety hormones, in particular glucagon-like-peptide-1 (GLP-1) and therefore DGAT inhibitors, in particular DGAT1 inhibitors, can also be used to prevent or treat a disease which can benefit from elevated levels of a satiety hormone, in particular GLP-1. Glucagon-like peptide 1 (GLP-1) is an intestinal hormone which generally stimulates insulin secretion during hyperglycemia, suppresses glucagon secretion, stimulates (pro) insulin biosynthesis and decelerates gastric emptying and acid secretion. GLP-1 is secreted from L cells in the small and large bowel following the ingestion of fat and proteins. GLP-1 has been suggested, among other indications, as a possible therapeutic agent for the management of type 2 non-insulin-dependent diabetes mellitus as well as related metabolic disorders, such as obesity.

Thus, by the present finding, a disease which can benefit from elevated levels of GLP-1 can be treated with small molecules (compared to large molecules such as proteins or protein-like compounds, e.g. GLP-1 analogues).

BACKGROUND PRIOR ART

WO 2006/034441 discloses heterocyclic derivatives and their use as stearoyl CoA desaturase inhibitors (SCD-1 inhibitors).
WO 2006/086445 relates to a combination therapy of a SCD-1 inhibitor and another drug to treat adverse weight gain.
WO 2006/004200 and JP2007131584 relate to urea and amino derivatives having DGAT inhibitory activity.
WO 2004/047755 relates to fused bicyclic nitrogen-containing heterocycles having DGAT inhibitory activity.
WO2005/072740 relates to an anorectic action of a compound having DGAT inhibitory activity.

DESCRIPTION OF THE INVENTION

The present invention relates to the use of a DGAT inhibitor for the manufacture of a medicament for the prevention or the treatment, in particular for the treatment, of a disease which can benefit from elevated levels of one or more satiety hormones, in particular GLP-1.

The present invention further relates to a compound of formula

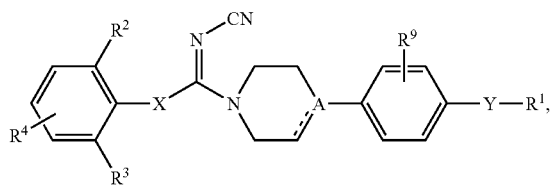

(I)

including any stereochemically isomeric form thereof, wherein
A represents CH or N;
X represents O or $NR^x$;
the dotted line represents an optional bond in case A represents a carbon atom;
Y represents a direct bond; $—NR^x—C(=O)—$; $—C(=O)—NR^x—$; $—NR^x—C(=O)—Z—$; $—NR^x—C(=O)—Z—NR^y—$; $—NR^x—C(=O)—Z—NR^y—C(=O)—$; $—NR^x—C(=O)—Z—NR^y—C(=O)—O—$; $—NR^x—C(=O)—Z—O—$; $—NR^x—C(=O)—Z—O—C(=O)—$; $—NR^x—C(=O)—Z—C(=O)—$; $—NR^x—C(=O)—Z—C(=O)—O—$; $—NR^x—C(=O)—O—Z—C(=O)—$; $—NR^x—C(=O)—O—Z—C(=O)—O—$; $—NR^x—C(=O)—O—Z—O—C(=O)—$; $—NR^x—C(=O)—Z—C(=O)—NR^y—$; $—NR^x—C(=O)—Z—NR^y—C(=O)—NR^y—$; $—C(=O)—Z—$; $—C(=O)—Z—O—$; $—C(=O)—NR^x—Z—$; $—C(=O)—NR^x—Z—O—$; $—C(=O)—NR^x—Z—C(=O)—O—$; $—C(=O)—NR^x—Z—O—C(=O)—$; $—C(=O)—O—Z—C(=O)—$; $—C(=O)—O—Z—NR^y—$; $—C(=O)—NR^x—Z—NR^y—$; $—C(=O)—NR^x—Z—NR^y—C(=O)—$; $—C(=O)—NR^x—Z—NR^y—C(=O)—O—$;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;
$R^x$ represents hydrogen or $C_{1-4}$alkyl;
$R^y$ represents hydrogen; $C_{1-4}$alkyl optionally substituted with $C_{3-6}$cycloalkyl or aryl or Het; $C_{2-4}$alkenyl; or $—S(=O)_p$-aryl;
$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; $aryl^1$; $aryl^1C_{1-6}$alkyl; $Het^1$; or $Het^1C_{1-6}$alkyl; provided that when Y represents $—NR^x—C(=O)—Z—$; $—NR^x—C(=O)—Z—NR^y—$; $—NR^x—C(=O)—Z—C(=O)—NR^y—$; $—C(=O)—Z—$; $—NR^x—C(=O)—Z—NR^y—C(=O)—NR^y—$; $—C(=O)—NR^x—Z—$; $—C(=O)—NR^x—O—Z—$; or $—C(=O)—NR^x—Z—NR^y—$; then $R^1$ may also represent hydrogen;
$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $—S(=O)_p—C_{1-4}$alkyl;
$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; $—S(=O)_p—C_{1-4}$alkyl; $R^6R^5N—C(=O)—$; $R^6R^5N—C_{1-6}$alkyl; $C_{3-6}$cycloalkyl; aryl; aryloxy; aryl$C_{1-4}$alkyl; aryl-C(=O)—$C_{1-4}$alkyl; aryl-C(=O)—$; Het; Het$C_{1-4}$alkyl; Het-C(=O)—$C_{1-4}$alkyl; Het-C(=O)—$; Het-O—$;
$R^5$ represents hydrogen; $C_{1-4}$alkyl optionally substituted with hydroxyl or $C_{1-4}$alkyloxy; $R^8R^7N—C_{1-4}$alkyl; $C_{1-4}$alkyloxy; Het; aryl; $R^8R^7N—C(=O)—C_{1-4}$alkyl;
$R^6$ represents hydrogen or $C_{1-4}$alkyl;
$R^7$ represents hydrogen; $C_{1-4}$alkyl; $C_{1-4}$alkylcarbonyl;
$R^8$ represents hydrogen or $C_{1-4}$alkyl; or
$R^7$ and $R^8$ may be taken together with the nitrogen to which they are attached to form a saturated monocyclic 5, 6 or 7-membered heterocycle which may further contain one or more heteroatoms each independently selected from O, S, $S(=O)_p$ or N; and which heterocycle may optionally be substituted with $C_{1-4}$alkyl;
$R^9$ represents hydrogen, halo, $C_{1-4}$alkyl, $C_{1-4}$alkyl substituted with hydroxyl;
aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl)amino; $—S(=O)_p—C_{1-4}$alkyl;
$aryl^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; amino; mono- or di($C_{1-6}$alkyl)amino; $R^6R^5N$—$C_{1-6}$ alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl $C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; amino; mono- or di($C_{1-6}$alkyl)amino; $R^6R^5N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—;

p represents 1 or 2;

a N-oxide thereof, a pharmaceutically acceptable salt thereof or a solvate thereof.

The present invention also relates to the use of a compound of formula (I) for the manufacture of a medicament for the prevention or the treatment of a disease which can benefit from elevated levels of one or more satiety hormones, in particular GLP-1, in particular the present invention relates to the use of a compound of formula (I) for the manufacture of a medicament for the treatment of a disease which can benefit from elevated levels of GLP-1.

The present invention further relates to the use of a compound of formula (I) for the manufacture of a medicament for the prevention or the treatment of a disease mediated by DGAT, in particular the present invention relates to the use of a compound of formula (I) for the manufacture of a medicament for the prevention or the treatment of a disease which can benefit from inhibition of DGAT, in particular for the treatment of a disease which can benefit from inhibition of DGAT, in particular DGAT1.

As used hereinbefore or hereinafter $C_{0-3}$alkyl as a group or part of a group defines straight or branched chain saturated hydrocarbon radicals having from 0 (then it represents a direct bond) to 3 carbon atoms such as methyl, ethyl, propyl, 1-methyl-ethyl; $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-5}$alkyl as a group or part of a group defines straight or branched chain saturated hydrocarbon radicals having from 1 to 5 carbon atoms such as the group defined for $C_{1-4}$alkyl and pentyl, 2-methylbutyl and the like; $C_{1-6}$alkyl as a group or part of a group defines straight or branched chain saturated hydrocarbon radicals having from 1 to 6 carbon atoms such as the group defined for $C_{1-4}$alkyl and for $C_{1-5}$alkyl and hexyl, 2-methylpentyl and the like; $C_{1-12}$alkyl as a group or part of a group defines straight or branched chain saturated hydrocarbon radicals having from 1 to 12 carbon atoms such as the group defined for $C_{1-6}$alkyl and heptyl, 2-methylheptyl and the like; $C_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl and the like; $C_{2-4}$alkenyl as a group or part of a group defines straight or branched chain hydrocarbon radicals having from 2 to 4 carbon atoms and having a double bond such as ethenyl, propenyl, butenyl and the like; $C_{2-6}$alkenyl as a group or part of a group defines straight or branched chain hydrocarbon radicals having from 2 to 6 carbon atoms and having a double bond such as the group defined for $C_{2-4}$alkenyl and pentenyl, hexenyl, 3-methylbutenyl and the like; $C_{2-6}$alkenediyl defines straight or branched chain bivalent hydrocarbon radicals having from 2 to 6 carbon atoms and having a double bond such as 1,2-ethenediyl, 1,3-propenediyl, 1,4-butenediyl, 1,5-pentenediyl and the like; $C_{2-6}$alkynyl defines straight and branched chain hydrocarbon radicals having from 2 to 6 carbon atoms and having a triple bond such as ethynyl, propynyl, butynyl, pentynyl, hexynyl and the like; $C_{2-6}$alkynediyl as a group or part of a group defines straight or branched chain bivalent hydrocarbon radicals having from 2 to 6 carbon atoms and having a triple bond such as 1,2-ethynediyl, 1,3-propynediyl, 1,4-butynediyl, 1,5-pentynediyl and the like; $C_{3-6}$cycloalkyl is generic to cyclopropyl, cyclobutyl, cyclopentyl and cyclohexyl.

The term halo is generic to fluoro, chloro, bromo and iodo. As used hereinbefore or hereinafter, polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoro-ethyl and the like. In case more than one halogen atoms are attached to a $C_{1-6}$alkyl group within the definition of polyhalo$C_{1-6}$alkyl, they may be the same or different.

As used herein before, the term (=O) forms a carbonyl moiety when attached to a carbon atom, a sulfoxide moiety when attached to a sulfur atom and a sulfonyl moiety when two of said terms are attached to a sulfur atom. Oxo means =O.

The radical Het or Het$^1$ as defined hereinabove may be an optionally substituted monocyclic non-aromatic or aromatic heterocycle containing at least one heteroatom, in particular 1, 2 or 3 heteroatoms, each independently selected from O, S, S(=O)$_p$ or N; or an optionally substituted bi- or tricyclic non-aromatic or aromatic heterocycle containing at least one heteroatom, in particular 1, 2, 3, 4 or 5 heteroatoms, each independently selected from O, S, S(=O)$_p$ or N. Examples of such unsubstituted monocyclic heterocycles comprise, but are not limited to, non-aromatic (fully saturated or partially saturated) or aromatic 4-, 5-, 6- or 7-membered monocyclic heterocycles such as for example azetidinyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, hexahydrodiazepinyl, pyrrolinyl, imidazolinyl, pyrazolinyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl and the like. Examples of such unsubstituted bicyclic or tricyclic heterocycles comprise, but are not limited to, non-aromatic (fully saturated or partially saturated) or aromatic 8- to 17-membered bicyclic or tricyclic heterocycles such as for example decahydroquinolinyl, octahydroindolyl, 2,3-dihydrobenzo furanyl, 1,3-benzodioxolyl, 2,3-dihydro-1,4-benzodioxinyl, indolinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl; isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like. Optional substituents for Het heterocycles are hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl) amino; —S(=O)$_p$—$C_{1-4}$alkyl. Optional substituents for Het$^1$ substituents are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; amino; mono- or di($C_{1-6}$alkyl)amino; $R^6R^5N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; arylC$_{1-4}$alkyl; aryl-C(=O)—; aryl-C(=O)—$C_{1-4}$alkyl; Het; HetC$_{1-4}$alkyl; Het-C(=O)—; Het-C(=O)—$C_{1-4}$alkyl; Het-O—.

When any variable occurs more than one time in any constituent (e.g. aryl, Het, aryl$^1$, Het$^1$), each definition is independent.

The term Het or Het$^1$ is meant to include all the possible isomeric forms of the heterocycles, for instance, pyrrolyl comprises 1H-pyrrolyl and 2H-pyrrolyl.

The carbocycles or heterocycles covered by the terms aryl, Het, aryl$^1$ or Het$^1$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

Lines drawn from substituents into ring systems indicate that the bond may be attached to any of the suitable ring atoms.

When Y is defined for instance as —NR$^x$—C(=O)—, this means that the nitrogen of NR$^x$ is linked to the phenyl moiety and the carbon atom of C(=O) is linked to the R$^1$ substituent. Thus the left part of the bivalent radical in the definition of Y is linked to the phenyl moiety and the right part of the bivalent radical in the definition of Y is linked to the R$^1$ substituent.

Some of the compounds of formula (I) may also exist in their tautomeric form. Such forms although not explicitly indicated in the above formula are intended to be included within the scope of the present invention.

Whenever used hereinbefore or hereinafter that substituents can be selected each independently out of a list of numerous definitions, such as for example for R$^2$ and R$^3$, all possible combinations are intended which are chemically possible.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted $C_{1-6}$alkylhalide, arylhalide, $C_{1-6}$alkyl-carbonylhalide, arylcarbonylhalide, or aryl$C_{1-6}$alkylhalide, e.g. methyliodide or benzyliodide. Other reactants with good leaving groups may also be used, such as for example $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

The term solvate comprises the hydrates and solvent addition forms which the compounds of formula (I) are able to form, as well as salts thereof. Examples of such forms are e.g. hydrates, alcoholates and the like.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, salts, and solvates may contain one or more centers of chirality and exist as stereo chemically isomeric forms.

The term "stereochemically isomeric forms" as used hereinbefore or hereinafter defines all the possible stereoisomeric forms which the compounds of formula (I), and their N-oxides, salts, or solvates may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts or solvates, substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Whenever used hereinafter, the term "compounds of formula (I)" or any subgroup thereof, is meant to also include their N-oxide forms, their salts, their stereochemically isomeric forms and their solvates. Of special interest are those compounds of formula (I) which are stereochemically pure.

A first embodiment of the present invention are those compounds of formula (I) having the following formula

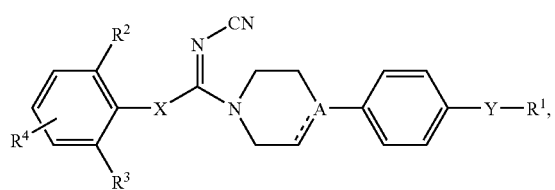

including any stereochemically isomeric form thereof, wherein

A represents CH or N;

X represents O or $NR^x$;

the dotted line represents an optional bond in case A represents a carbon atom;

Y represents a direct bond; $-NR^x-C(=O)-$; $-C(=O)-NR^x-$; $-NR^x-C(=O)-Z-$; $-NR^x-C(=O)-Z-NR^y-$; $-NR^x-C(=O)-Z-NR^y-C(=O)-$; $-NR^x-C(=O)-Z-NR^y-C(=O)-O-$; $-NR^x-C(=O)-Z-O-$; $-NR^x-C(=O)-Z-O-C(=O)-$; $-NR^x-C(=O)-Z-C(=O)-$; $-NR^x-C(=O)-Z-C(=O)-O-$; $-NR^x-C(=O)-O-Z-C(=O)-$; $-NR^x-C(=O)-O-Z-C(=O)-O-$; $-NR^x-C(=O)-O-Z-O-C(=O)-$; $-NR^x-C(=O)-Z-C(=O)-NR^y-$; $-NR^x-C(=O)-Z-NR^y-C(=O)-NR^y-$; $-C(=O)-Z-$; $-C(=O)-Z-O-$; $-C(=O)-NR^x-Z-$; $-C(=O)-NR^x-Z-O-$; $-C(=O)-NR^x-Z-C(=O)-O-$; $-C(=O)-NR^x-Z-O-C(=O)-$; $-C(=O)-NR^x-O-Z-$; $-C(=O)-NR^x-Z-NR^y-$; $-C(=O)-NR^x-Z-NR^y-C(=O)-$; $-C(=O)-NR^x-Z-NR^y-C(=O)-O-$;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$alkenyl; or $S(=O)_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; aryl$^1$; aryl$^1C_{1-6}$alkyl; Het$^1$; or Het$^1C_{1-6}$alkyl; provided that when Y represents $-NR^x-C(=O)-Z-$; $-NR^x-C(=O)-Z-NR^y-$; $-NR^x-C(=O)-Z-C(=O)-NR^y-$; $-C(=O)-Z-$; $-NR^x-C(=O)-Z-NR^y-C(=O)-NR^y-$; $-C(=O)-NR^x-Z-$; $-C(=O)-NR^x-O-Z-$; or $-C(=O)-NR^x-Z-NR^y-$; then $R^1$ may also represent hydrogen;

$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $-S(=O)_p-C_{1-4}$alkyl;

$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $-S(=O)_p-C_{1-4}$alkyl; $R^6R^5N-C(=O)-$; $R^6R^5N-C_{1-4}$alkyl; $C_{3-6}$cycloalkyl; aryl; aryloxy; aryl$C_{1-4}$alkyl; aryl-$C(=O)-$; Het; HetC$_{1-4}$alkyl; Het-$C(=O)-$; Het-$O-$;

$R^5$ represents hydrogen; $C_{1-4}$alkyl optionally substituted with hydroxyl or $C_{1-4}$alkyloxy; $R^8R^7N-C_{1-4}$alkyl; $C_{1-4}$alkyloxy; Het; aryl; $R^8R^7N-C(=O)-C_{1-4}$alkyl;

$R^6$ represents hydrogen or $C_{1-4}$alkyl;

$R^7$ represents hydrogen; $C_{1-4}$alkyl; $C_{1-4}$alkylcarbonyl;

$R^8$ represents hydrogen or $C_{1-4}$alkyl; or $R^7$ and $R^8$ may be taken together with the nitrogen to which they are attached to form a saturated monocyclic 5, 6 or 7-membered heterocycle which may further contain one or more heteroatoms selected from O, S, $S(=O)_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di ($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl) amino; $-S(=O)_p-C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-$C(=O)-$; hydroxy$C_{1-6}$alkyl optionally substituted with aryl or aryl-$C(=O)-$; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-$NR^x-$; aryl-$NR^x-$; Het-$NR^x-$; $C_{3-6}$cycloalkyl $C_{1-4}$alkyl-$NR^x-$; aryl$C_{1-4}$alkyl-$NR^x-$; Het$C_{1-4}$alkyl-$NR^x-$; $-S(=O)_p-C_{1-4}$alkyl; $C_{3-6}$cycloalkyl; $C_{3-6}$cycloalkyl$C_{1-4}$alkyl; $C_{3-6}$cycloalkyl-$C(=O)-$; aryl; aryloxy; aryl$C_{1-4}$alkyl; aryl-$C(=O)-$; Het; Het$C_{1-4}$alkyl; Het-$C(=O)-$; Het-$O-$;

Het represents a monocyclic non-aromatic or aromatic heterocycle containing at least one heteroatom selected from O, S, $S(=O)_p$ or N; or a bicyclic or tricyclic non-aromatic or aromatic heterocycle containing at least one heteroatom selected from O, S, $S(=O)_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $-S(=O)_p-C_{1-4}$alkyl;

Het$^1$ represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with aryl-C(=O)—; hydroxyC$_{1-6}$alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxy-carbonyl wherein C$_{1-6}$alkyl may optionally be substituted with aryl; cyano; aminocarbonyl; mono- or di(C$_{1-4}$alkyl)aminocarbonyl; C$_{1-6}$alkylcarbonyl; nitro; amino; mono- or di(C$_{1-6}$alkyl)amino; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—; Het; HetC$_{1-4}$alkyl; Het-C(=O)—; Het-O—;

p represents 1 or 2;

a N-oxide thereof, a pharmaceutically acceptable salt thereof or a solvate thereof.

A second embodiment of the present invention are those compounds of formula (I) or any subgroup thereof as mentioned hereinbefore as embodiment, wherein X represents NR$^x$, in particular NH.

A third embodiment of the present invention are those compounds of formula (I) or, whenever possible, any subgroup thereof as mentioned hereinbefore as embodiment, wherein X represents O.

A fourth embodiment of the present invention are those compounds of formula (I) or, whenever possible, any subgroup thereof as mentioned hereinbefore as embodiment wherein A represents N.

A fifth embodiment of the present invention are those compounds of formula (I) or, whenever possible, any subgroup thereof as mentioned hereinbefore as embodiment wherein A represents CH, in particular wherein A represents CH and the dotted line does not represent a bond.

A sixth embodiment of the present invention are those compounds of formula (I) or any subgroup thereof as mentioned hereinbefore as embodiment wherein Y represents —NR$^x$—C(=O)—; —NR$^x$—C(=O)—Z—; —NR$^x$—C(=O)—Z—NR$^y$—; —NR$^x$—C(=O)—Z—O—C(=O)—; in particular wherein Y represents —NR$^x$—C(=O)— or —NR$^x$—C(=O)—Z— with Z representing C$_{1-6}$alkanediyl.

A seventh embodiment of the present invention are those compounds of formula (I) or, whenever possible, any subgroup thereof as mentioned hereinbefore as embodiment wherein Y represents a direct bond, in particular wherein Y represents a direct bond and R$^1$ represents Het$^1$.

An eighth embodiment of the present invention are those compounds of formula (I) or, whenever possible, any subgroup thereof as mentioned hereinbefore as embodiment wherein Y represents —NR$^x$—C(=O)—, in particular wherein Y represents —NR$^x$—C(=O)— and R$^1$ represents Aryl$^1$ or Het$^1$.

A ninth embodiment of the present invention are those compounds of formula (I) or, whenever possible, any subgroup thereof as mentioned hereinbefore as embodiment wherein Y represents —NR$^x$—C(=O)—Z—NR$^y$—, in particular wherein Y represents —NR$^x$—C(=O)—Z—NR$^y$— and R$^1$ represents Aryl$^1$ or Het$^1$.

A tenth embodiment of the present invention are those compounds of formula (I) or, whenever possible, any subgroup thereof as mentioned hereinbefore as embodiment wherein Y represents —NR$^x$—C(=O)—Z—C(=O)—O— or —NR$^x$—C(=O)—Z—O—C(=O)—, in particular —NR$^x$—C(=O)—Z—O—C(=O)—.

An eleventh embodiment of the present invention are those compounds of formula (I) or, whenever possible, any subgroup thereof as mentioned hereinbefore as embodiment wherein R$^2$ or R$^3$ each independently represent hydrogen, halo or C$_{1-6}$alkyl, in particular both R$^2$ and R$^3$ represent halo, more in particular both R$^2$ and R$^3$ represent chloro or fluoro.

A twelfth embodiment of the present invention are those compounds of formula (I) or, whenever possible, any subgroup thereof as mentioned hereinbefore as embodiment wherein R$^4$ is placed in para position.

A thirteenth embodiment of the present invention are those compounds of formula (I) or, whenever possible, any subgroup thereof as mentioned hereinbefore as embodiment wherein R$^4$ represents hydrogen; carboxyl; C$_{1-6}$alkyloxycarbonyl; amino; mono- or di(C$_{1-4}$alkyl)amino; R$^6$R$^5$N—C(=O)—; R$^6$R$^5$N—C$_{1-6}$alkyl; Het-C(=O)— or HetC$_{1-4}$alkyl, in particular Het-C(=O)— or HetC$_{1-4}$alkyl.

A fourteenth embodiment of the present invention are those compounds of formula (I) or, whenever possible, any subgroup thereof as mentioned hereinbefore as embodiment wherein R$^4$ is placed in para position and represents hydrogen; carboxyl; C$_{1-6}$alkyloxy-carbonyl; amino; mono- or di(C$_{1-4}$alkyl)amino; R$^6$R$^5$N—C(=O)—; R$^6$R$^5$N—C$_{1-6}$alkyl; Het-C(=O)— or HetC$_{1-4}$alkyl, in particular Het-C(=O)— or HetC$_{1-4}$alkyl.

A fifteenth embodiment of the present invention are those compounds of formula (I) or, whenever possible, any subgroup thereof as mentioned hereinbefore as embodiment wherein p represents 2.

A sixteenth embodiment of the present invention are those compounds of formula (I) or, whenever possible, any subgroup thereof as mentioned hereinbefore as embodiment wherein R$^1$ represents hydrogen; C$_{1-12}$alkyl; aryl$^1$ or Het$^1$; in particular Aryl$^1$ or Het$^1$; more in particular Aryl$^1$; more in particular optionally substituted phenyl wherein the optional substituent is preferably selected from aryl, Het or C$_{1-6}$alkyloxy; even more in particular phenyl.

A seventeenth embodiment of the present invention are those compounds of formula (I) or, whenever possible, any subgroup thereof as mentioned hereinbefore as embodiment wherein Z represents C$_{1-6}$alkanediyl.

An eighteenth embodiment of the present invention are those compounds of formula (I) or, whenever possible, any subgroup thereof as mentioned hereinbefore as embodiment wherein Rx represents hydrogen.

A nineteenth embodiment of the present invention are those compounds of formula (I) or, whenever possible, any subgroup thereof as mentioned hereinbefore as embodiment wherein R$^y$ represents hydrogen.

A twentieth embodiment of the present invention are those compounds of formula (I) or, whenever possible, any subgroup thereof as mentioned hereinbefore as embodiment wherein R$^9$ represents hydrogen.

A twenty first embodiment of the present invention are those compounds of formula (I) or, whenever possible, any subgroup thereof as mentioned hereinbefore as embodiment wherein R$^9$ represents halo, C$_{1-4}$alkyl, C$_{1-4}$alkyl substituted with hydroxyl.

A twenty second embodiment of the present invention are those compounds of formula (I) or any subgroup thereof as mentioned hereinbefore as embodiment wherein one or more, preferably all, of the following restrictions apply:
a) X represents NH;
b) $R^2$ represents hydrogen, halo or $C_{1-6}$alkyl; in particular halo; more in particular chloro;
c) $R^3$ represents hydrogen, halo or $C_{1-6}$alkyl; in particular halo; more in particular chloro;
d) $R^4$ represents hydrogen;
e) A represents N;
f) the dotted line does not represent an additional bond;
g) Y represents —$NR^x$—C(=O)—Z—;
h) Z represents $C_{1-6}$alkanediyl;
i) $R^1$ represents aryl$^1$; in particular optionally substituted phenyl; more in particular phenyl.
j) Rx represents hydrogen.

A twenty third embodiment of the present invention are those compounds of formula (I) or any subgroup thereof as mentioned hereinbefore as embodiment wherein one or more, preferably all, of the following restrictions apply:
a) X represents NH or O;
b) $R^2$ represents hydrogen, halo or $C_{1-6}$alkyl; in particular halo; more in particular chloro or fluoro;
c) $R^3$ represents hydrogen, halo or $C_{1-6}$alkyl; in particular halo; more in particular chloro or fluoro;
d) $R^4$ represents hydrogen; carboxyl; $C_{1-6}$alkyloxycarbonyl; Het-C(=O)— or Het$C_{1-4}$alkyl, in particular Het-C(=O)— or Het$C_{1-4}$alkyl;
e) A represents N;
f) the dotted line does not represent a bond;
g) Y represents —$NR^x$—C(=O)—; —$NR^x$—C(=O)—Z—, —$NR^x$—C(=O)—Z—$NR^y$—;
—$NR^x$—C(=O)—Z—O—C(=O)—;
h) Z represents $C_{1-6}$alkanediyl;
i) $R^1$ represents hydrogen; $C_{1-12}$alkyl; aryl$^1$ or Het$^1$; in particular aryl$^1$; more in particular optionally substituted phenyl wherein the optional substituent is preferably selected from aryl, Het or $C_{1-6}$alkyloxy; more in particular phenyl;
j) $R^x$ represents hydrogen;
k) $R^y$ represents hydrogen;
l) $R^9$ represents hydrogen;
m) $R^4$ is placed in para position.

Preferred compounds are selected from

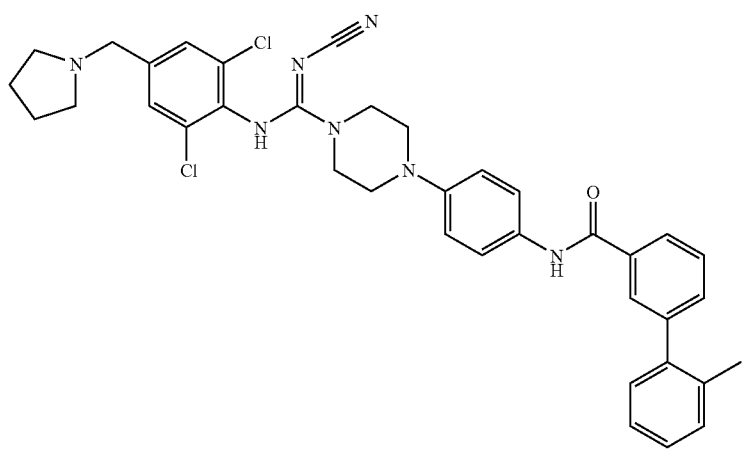

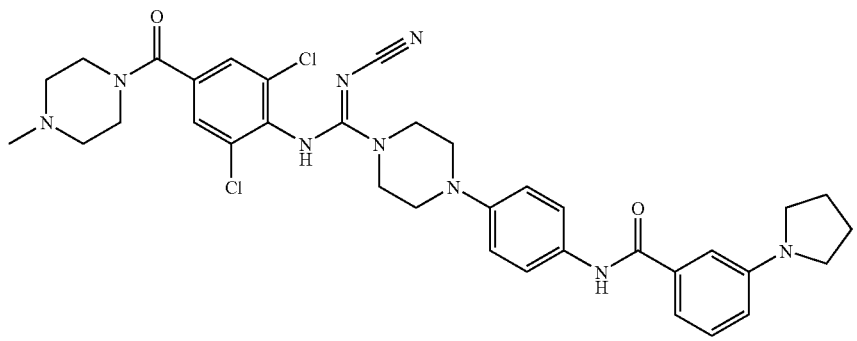

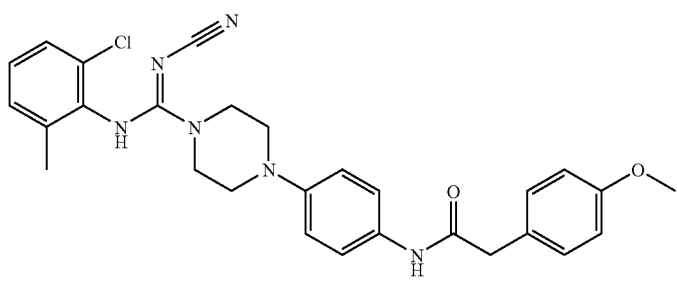

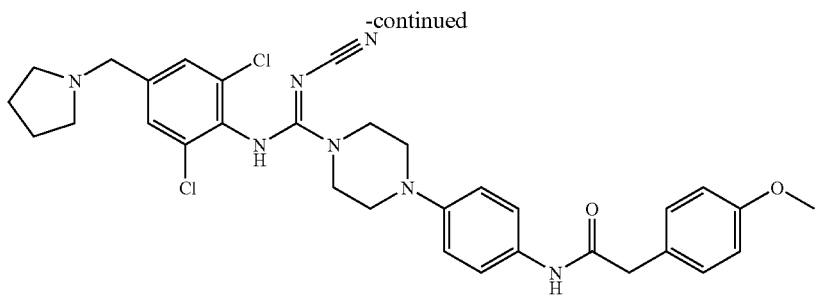

a N-oxide thereof, a pharmaceutically acceptable salt thereof or a solvate thereof.

In general, compounds of formula (I) wherein X represents NH, said compounds being represented by formula (I-a), can be prepared by reacting an intermediate of formula (II) with cyanamide, in particular lead cyanamide, in the presence of a suitable solvent, such as for example N,N-dimethylformamide.

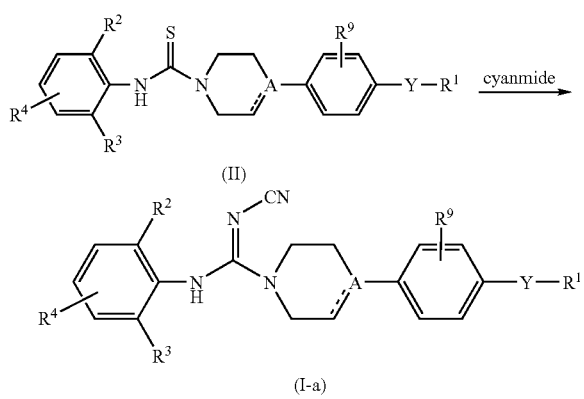

Compounds of formula (I) wherein X represents O, said compounds being represented by formula (I-b), can be prepared by reacting an intermediate of formula (III) wherein $W_1$ represents a suitable leaving group, such as for example phenoxy, with an intermediate of formula (IV) in the presence of a suitable solvent, such as for example tetrahydrofuran.

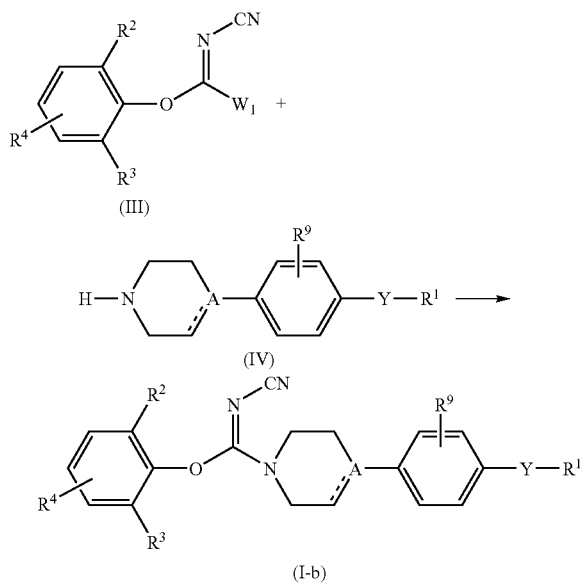

Compounds of formula (I-b) can be converted into a compound of formula (I-a) by reaction with an intermediate of formula (V) in the presence of a suitable strong base, such as for example sodium hydride, and a suitable solvent, such as for example dioxane.

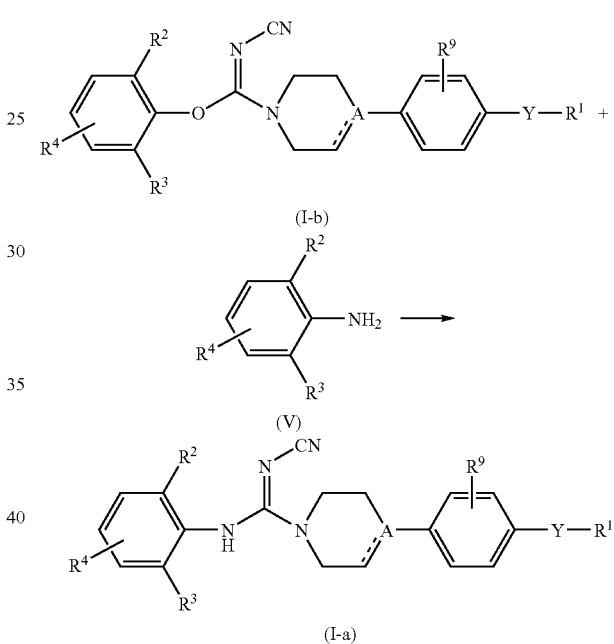

Compounds of formula (I) wherein Y comprises —$NR^x$—C(=O)—, said compounds being represented by formula (I-c), wherein $Y^1$ represents the remainder of the linker Y including a direct bond, can be prepared by reacting an intermediate of formula (XIX) with an intermediate of formula (XIII) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazolium-hexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, tetrahydrofuran or dichloromethane, and optionally in the presence of a suitable base, such as for example N,N-diisopropyl-ethanamine or N,N-diethyl-ethanamine.

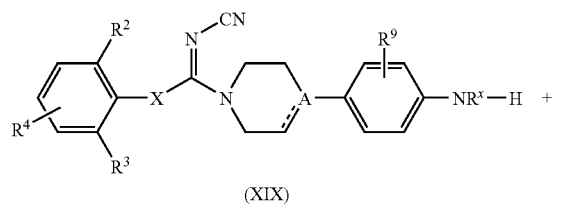

(XIX)

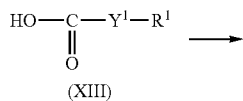

(XIII)

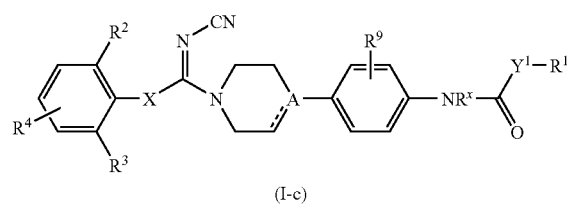

(I-c)

Compounds of formula (I-c) can also be prepared by reacting an intermediate of formula (XIX) with an intermediate of formula (XX) wherein $W_1$ represents a suitable leaving group, such as for example halo, e.g. chloro and the like, in the presence of a suitable base, such as for example sodium hydride, sodium bicarbonate, N,N-diisopropyl-ethanamine or N,N-diethyl-ethanamine, and a suitable solvent, such as for example N,N-dimethylformamide, dichloromethane, acetonitrile or tetrahydrofuran

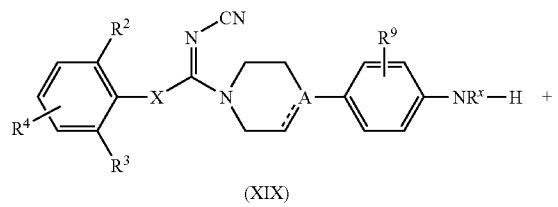

(XIX)

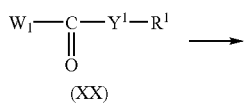

(XX)

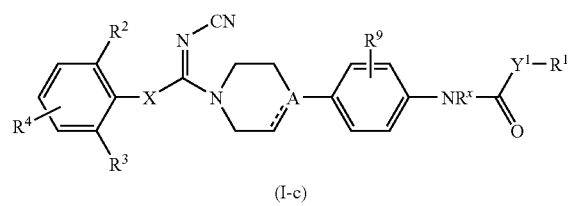

(I-c)

Compounds of formula (I) wherein Y represents —$NR^x$—C(=O)—Z—$NR^y$—, said compounds being represented by formula (I-d), can be prepared by reacting an intermediate of formula (XXI) wherein $W_2$ represents a suitable leaving group, such as for example halo, e.g. chloro, bromo and the like, with an intermediate of formula (XXII) in the presence of a suitable base, such as for example $Na_2CO_3$, $K_2CO_3$, and a suitable solvent, such as for example N,N-dimethylformamide.

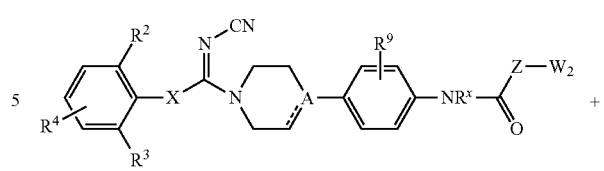

(XIX)

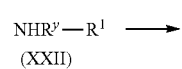

(XXII)

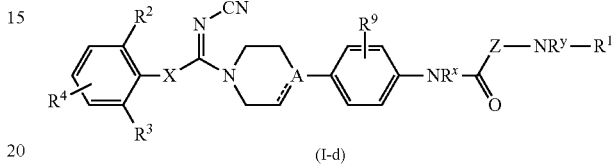

(I-d)

Compounds of formula (I) wherein Y represents —$NR^x$—C(=O)—Z— and $R^1$ represents an optionally substituted monocyclic saturated heterocycle linked with a nitrogen atom to Z, said $R^1$ being represented by $R^{1a}$, and said compounds being represented by formula (I-e), can be prepared by reacting an intermediate of formula (XXI) with an intermediate of formula (XXII) in the presence of a suitable base, such as for example N,N-diisopropyl-ethanamine or N,N-diethyl-ethanamine, and a suitable solvent, such as for example acetonitrile or tetrahydrofuran.

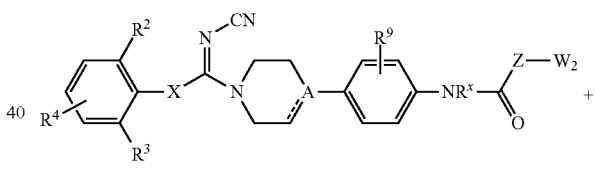

(XXI)

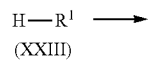

(XXIII)

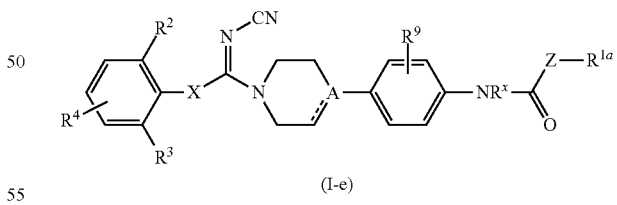

(I-e)

Compounds of formula (I) wherein $R^1$ is substituted with $NH_2$, said $R^1$ being represented by $R^{1'}$—$NH_2$, and said compounds being represented by formula (I-f), can be prepared by deprotecting an intermediate of formula (XXIV) wherein P represents a suitable protecting group, such as for example tertiair butyloxycarbonyl, in the presence of a suitable acid, such as for example trifluoroacteic acid, and in the presence of a suitable solvent, such as for example dichloromethane. The intermediate of formula (XXIV)) can be prepared according to one of the above reactions.

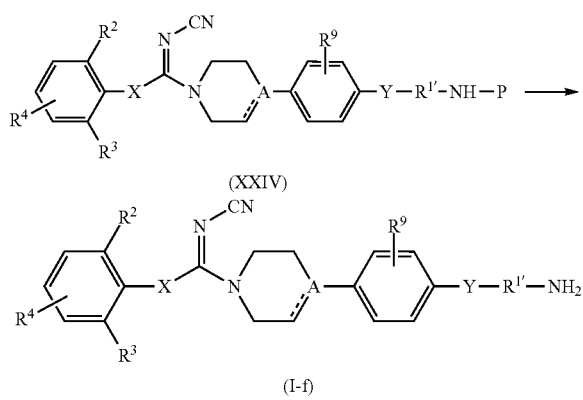

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$ is unsubstituted, can be converted into a compound wherein $R^1$ contains a $C_{1-4}$alkyl-$S(=O)_p$— substituent, by reaction with $C_{1-4}$alkyl-$S(=O)_p$—$W_2$ wherein $W_2$ represents a suitable leaving group, such as for example halo, e.g. chloro and the like, in the presence of a suitable base, such as for example N,N-diethylethanamine, and in the presence of a suitable solvent, such as for example acetonitrile.

Compounds of formula (I) wherein $R^1$ contains a $C_{1-6}$alkyloxycarbonyl substituent, can be converted into a compound of formula (I) wherein $R^1$ contain a carboxyl substituent, by reaction with a suitable base, such as for example sodium hydroxide, in the presence of a suitable solvent, such as for example dioxane.

Compounds of formula (I) wherein $R^1$ contains a $C_{1-6}$alkyloxycarbonyl substituent, can also be converted into a compound of formula (I) wherein $R^1$ contains a $CH_2$—OH substituent, by reaction with a suitable reducing agent, such as for example $LiBH_4$, in the presence of a suitable solvent, such as for example tetrahydrofuran or dioxane.

Compounds of formula (I) wherein $R^1$ contains a $C_{1-6}$alkyloxycarbonyl substituent, can also be converted into a compound of formula (I) wherein $R^1$ is unsubstituted by reaction with a suitable acid, such as for example hydrochloric acid and the like.

Compounds of formula (I) wherein $R^1$ contains a $C_{1-5}$alkyl-carbonyl substituent, can be converted into a compound of formula (I) wherein $R^1$ contains a $C_{1-5}$alkyl-CH(OH)— substituent, by reaction with a suitable reducing agent, such as for example $NaBH_4$, in the presence of a suitable solvent, such as for example an alcohol, e.g. methanol.

Compounds of formula (I) wherein $R^1$ contains a $C_{1-6}$alkyloxy substituent, can be converted into a compound of formula (I) wherein $R^1$ contains a OH substituent, by reaction with a suitable reducing agent, such as for example $BBr_3$, in the presence of a suitable solvent, such as for example dichloromethane or dichloroethane.

Compounds of formula (I) wherein $R^y$ represents allyl, can be converted into a compound of formula (I) wherein $R^y$ represents hydrogen, by reaction with a suitable catalyst, such as for example $Pd(PPh_3)_4$, and a suitable nucleophilic agent, such as for example

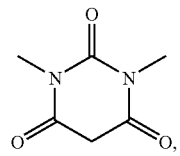

in the presence of a suitable solvent, such as for example dichloroethane.

Compounds of formula (I) wherein $R^y$ represents —$S(=O)_p$-aryl wherein aryl is nitro-substituted phenyl, can be converted into a compound of formula (I) wherein $R^y$ represents hydrogen, by reaction with LiOH and HS—$CH_2$—C(=O)—OH in the presence of a suitable solvent, such as for example N,N-dimethylformamide.

Compounds of formula (I) wherein $R^1$ contains a $C_{1-6}$alkyloxy substituent or $R^2$, $R^3$ or $R^4$ represents $C_{1-6}$alkyloxy, can be converted into a compound of formula (I) wherein $R^1$ contains a OH substituent or $R^2$, $R^3$ or $R^4$ represents OH, by reaction with a suitable reducing agent, such as for example $BBr_3$, in the presence of a suitable solvent, such as for example dichloromethane or dichloroethane.

Compounds of formula (I) wherein $R^1$ contains a carboxyl substituent or $R^4$ represents carboxyl, can be converted into a compound of formula (I) wherein $R^1$ contains a Het-C(=O)— substituent or $R^4$ represents Het-C(=O)— wherein Het represents an optionally substituted monocyclic saturated heterocycle containing at least one N atom, said heterocycle being linked via the N atom to the C(=O) group, by reaction with said heterocycle in the presence a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-) 3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction can also be performed as a fast synthesis reaction thereby using appropriate reagents well-known for fast synthesis, such as for example dicyclohexylcarbodiimide (DCC) or carbonyl diimidazole (CDI), linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene.

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography or SCF (Super Critical Fluid) chromatography, in particular using a chiral stationary phase.

Some of the intermediates and starting materials are known compounds and may be commercially available or may be prepared according to art-known procedures.

Intermediates of formula (II) can be prepared by reacting an intermediate of formula (IV) with an intermediate of formula (VI) in the presence of a suitable solvent, such as for example tetrahydrofuran

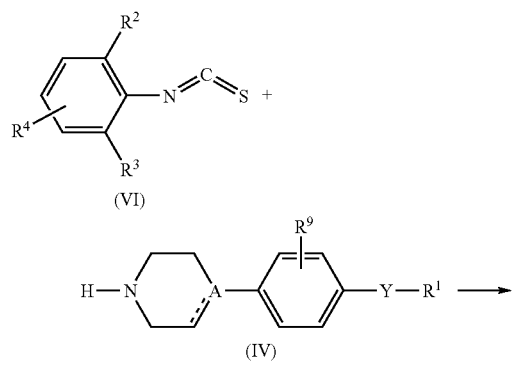

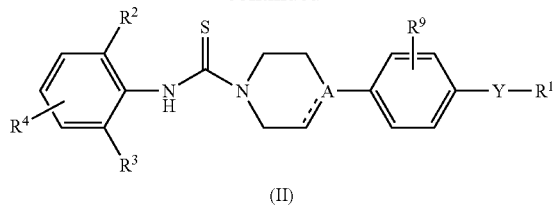

Intermediates of formula (IV) wherein Y comprises —NH—C(=O)—, said intermediates being represented by formula (IV-a), wherein $Y^1$ represents the remainder of the linker Y including a direct bond, can be prepared according to the following reaction scheme wherein an intermediate of formula (VII) wherein P represents a suitable protecting group, such as for example benzyloxycarbonyl or tertiair butyloxy or benzyl, and wherein $W_3$ represents a suitable leaving group, such as for example halo, e.g. chloro and the like, with an intermediate of formula (VIII) in the presence of a suitable base, such as for example $NaHCO_3$, and a suitable solvent, such as for example dichloromethane, resulting in an intermediate of formula (IX), followed in a next step by hydrogenating ($H_2$) said intermediate of formula (IX) in the presence of a suitable catalyst, such as for example platinum on charcoal, and a suitable solvent, such as for example tetrahydrofuran, and an alcohol, e.g. methanol, resulting in an intermediate of formula (X). In a next step, said intermediate of formula (X) is reacted with an intermediate of formula (XI) wherein $W_4$ represents a suitable leaving group, such as for example halo, e.g. chloro and the like, in the presence of a suitable base, such as for example $NaHCO_3$, and a suitable solvent, such as for example acetonitrile, resulting in an intermediate of formula (XII), which is deprotected in a next step in the presence of $H_2$, a suitable catalyst, such as for example palladium on charcoal, and a suitable solvent, such as for example an alcohol, e.g. methanol, and optionally in the presence of a suitable acid, such as for example methanesulfonic acid; or in the presence of a suitable acid, such as for example trifluoroacteic acid, and a suitable solvent, such as for example dichloromethane; or in the presence of ammonium formate, a suitable catalyst, such as for example palladium on charcoal, and a suitable solvent, such as for example an alcohol, e.g. methanol.

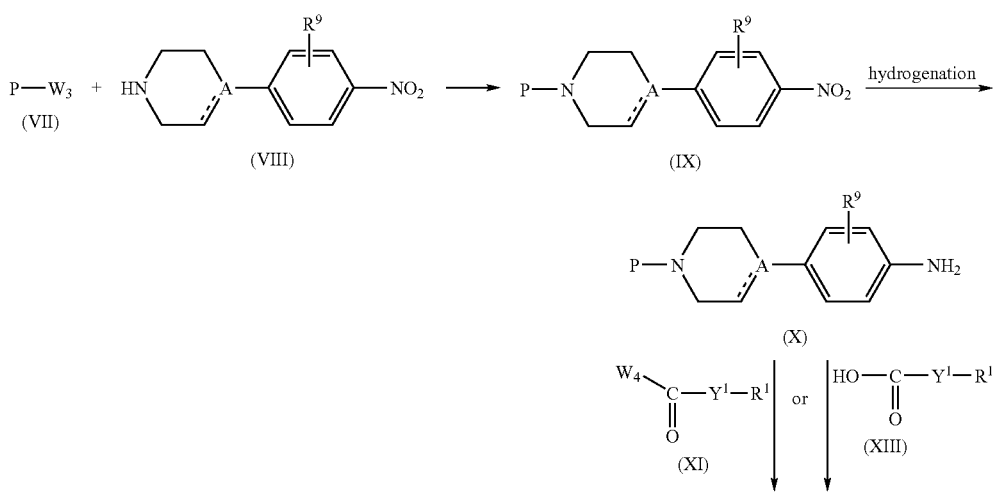

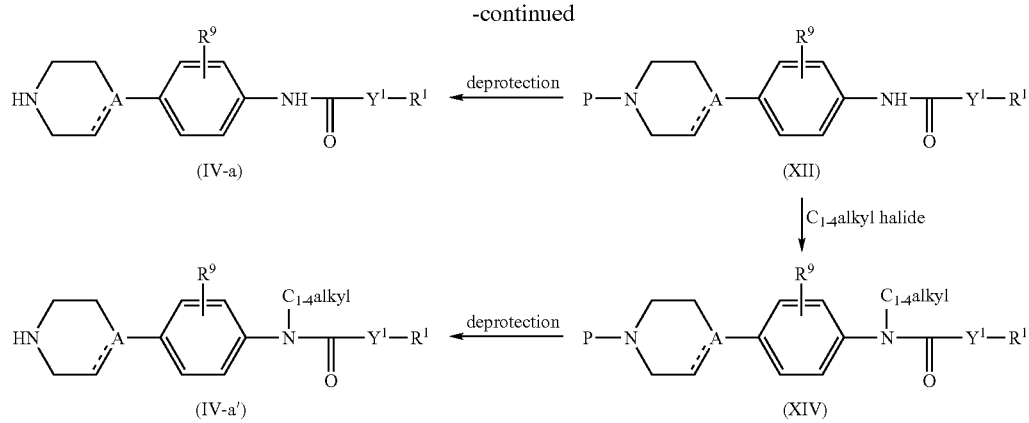

In the above reaction scheme, the intermediate of formula (X) can also react with an intermediate of formula (XIII) in the presence of a suitable activating agent, such as for example $SOCl_2$ or $Cl-C(=O)-C(=O)-Cl$, a suitable base, such as for example N,N-diethyl-ethanamine or N,N-diisopropyl-ethanamine, and a suitable solvent, such as for example dichloromethane or N,N-dimethylformamide. Or an intermediate of formula (XIII) can react with an intermediate of formula (X) in the presence of a suitable dehydrating (coupling) agent, such as for example N'-(ethylcarbonimidoyl)-N,N-dimethyl-1,3-propanediamine monohydrochloride (EDCI), dicyclohexyl-carbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

The intermediate of formula (XII) can also react with an $C_{1-4}$alkyl halide, e.g. $CH_3I$, in the presence of a suitable base, such as for example NaH, and a suitable solvent, such as for example N,N-dimethylformamide, to form an intermediate of formula (XV) which can be deprotected according to the above described protocol to result in an intermediate of formula (IV-a').

Intermediates of formula (XIII) can be prepared by hydrolizing an intermediate of formula (XV) with a suitable base, such as for example potassium hydroxide or sodium hydroxide, in the presence of a suitable solvent, such as for example water, tetrahydrofuran or an alcohol, e.g. methanol.

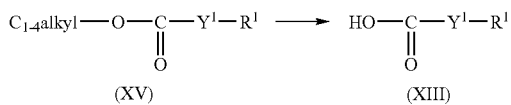

Intermediates of formula (XV) wherein $R^1$ represents $Het^1$ wherein said $Het^1$ is an optionally substituted heterocycle further substituted with either optionally substituted phenyl or an optionally substituted heterocycle, can be prepared by reacting the protected optionally substituted heterocycle with optionally substituted phenyl in the presence of a suitable catalyst, such as for example palladium acetate, in the presence of a suitable catalyst ligand, such as for example 1,1'-(1,5-pentanediyl)-bis[1,1'-diphenylphosphine], a suitable base, such as for example potassium acetate, and a suitable solvent, such as for example N-methyl-pyrrolidin-2-one; or by reacting the protected optionally substituted heterocycle with optionally substituted phenyl carrying a suitable leaving group, such as for example halo, e.g. bromo, iodo and the like, in the presence of a suitable catalyst, such as for example palladium acetate, in the presence of a suitable catalyst ligand, such as for example 1,3-propanediylbis[diphenylphosphine], a suitable base, such as for example potassium acetate or cesium carbonate, and a suitable solvent, such as for example N-methyl-pyrrolidin-2-one; or by reacting the protected optionally substituted heterocycle with an optionally substituted heterocycle carrying a suitable leaving group, such as for example halo, e.g. bromo, iodo and the like, in the presence of a suitable catalyst, such as for example palladium acetate, in the presence of a suitable catalyst ligand, such as for example 1,3-propanediylbis[diphenylphosphine], a suitable base, such as for example potassium acetate or cesium carbonate, and a suitable solvent, such as for example N-methyl-pyrrolidin-2-one.

Intermediates of formula (XV) wherein $R^1$ represents an optionally substituted phenyl further substituted with either optionally substituted phenyl or an optionally substituted heterocyle, can be prepared accordingly.

Intermediates of formula (XV) wherein $Y^1$ contains a $NR^y$ wherein $R^y$ represents $C_{2-4}$alkenyl, can be prepared from the corresponding intermediate wherein $R^y$ represents hydrogen, by reaction with $C_{2-4}$alkenyl-$W_5$ wherein $W_5$ represents a suitable leaving group, such as for example halo, e.g. iodo and the like, in the presence of a suitable base, such as for example $K_2CO_3$ or N,N-diisopropyl-ethanamine, and a suitable solvent, such as for example N,N-dimethylformamide or an alcohol, e.g. ethanol.

Intermediates of formula (XV) wherein $Y^1$ contains a $NR^y$ wherein $R^y$ represents —S(=O)$_p$-aryl, can be prepared from the corresponding intermediate wherein $R^y$ represents hydrogen, by reaction with $W_6$—S(=O)$_p$-aryl wherein $W_6$ represents a suitable leaving group, such as for example halo, e.g. chloro and the like, in the presence of a suitable base, such as for example N,N-diethyl-ethanamine, and a suitable solvent, such as for example acetonitrile.

Intermediates of formula (XIII) wherein $Y^1$ represents —Z—$NR^y$—C(=O)—$NR^y$—, said intermediates being represented by formula (XIII-a), can be prepared by reacting an intermediate of formula (XVI) with an intermediate of formula (XVII) in the presence of a suitable base, such as for example N,N-diethyl-ethanamine, and a suitable solvent, such as for example acetonitrile, followed by deprotecting the resulting intermediate of formula (XVIII) with a suitable base, such as for example KOH, in the presence of a suitable solvent, such as for example water and an alcohol, e.g. ethanol.

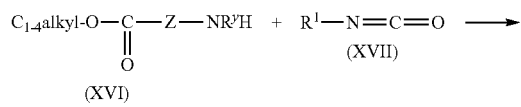

(XVI) + (XVII)

-continued

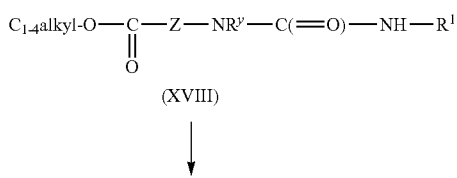

(XVIII)

↓

HO—C(=O)—Z—$NR^y$—C(=O)—NH—$R^1$ (XIII-a)

Intermediates of formula (XIX) wherein $R^x$ represents hydrogen and X represents NH, said intermediates being represented by formula (XIX-a) can be prepared by reacting an intermediate of formula (XXV) with diphenyl N-cyanocarbonimidate in the presence of a suitable solvent, such as for example tetrahydrofuran. The resulting intermediate of formula (XXVI) can then be reacted in a next step with an intermediate of formula (V) in the presence of NaH and a suitable solvent, such as for example N,N-dimethylformamide. The resulting intermediate of formula (XXVII) can then be hydrogenated in the presence of a suitable catalyst, such as for example platina on charcoal, a suitable catalyst poison, such as for example a thiophene solution, and a suitable solvent, such as for example tetrahydrofuran or an alcohol, e.g. methanol to obtain an intermediate of formula (XIX-a).

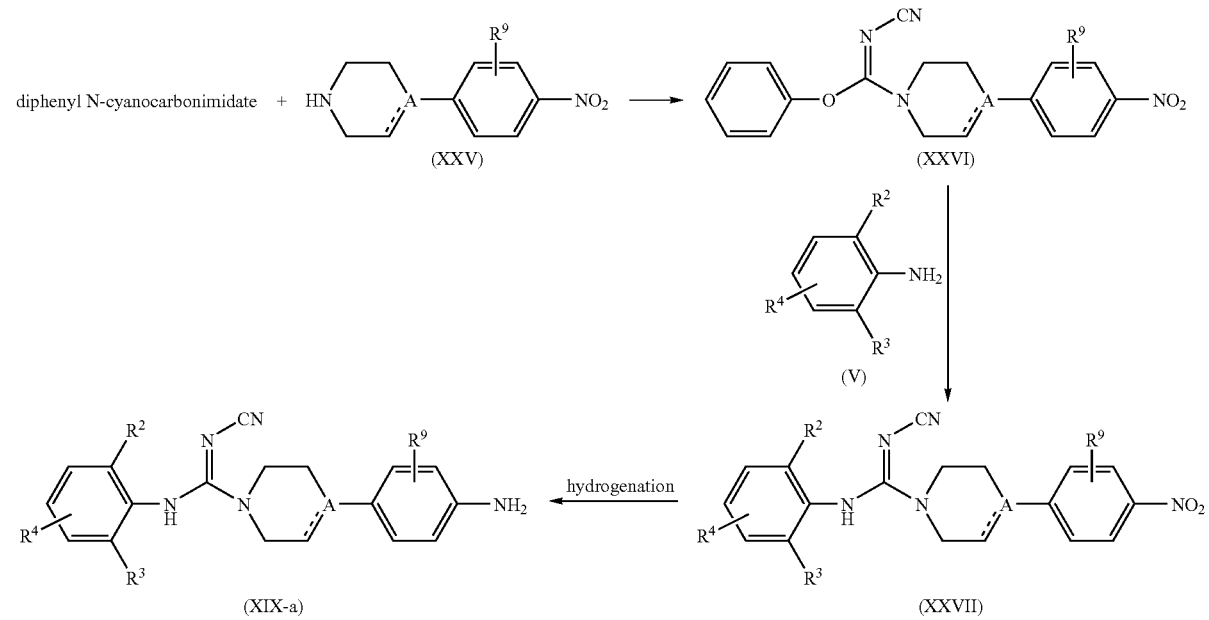

Intermediates of formula (XIX-a) can also be prepared by reacting an intermediate of formula (V) with diphenyl N-cyanocarbonimidate in the presence of a suitable solvent, such as for example pyridine. The resulting intermediate of formula ((XXVIII) can then be reacted with an intermediate of formula (XXV) in the presence of a suitable solvent, such as for example pyridine, resulting in an intermediate of formula (XXVII) which can be converted into an intermediate of formula (XIX-a) as described above.

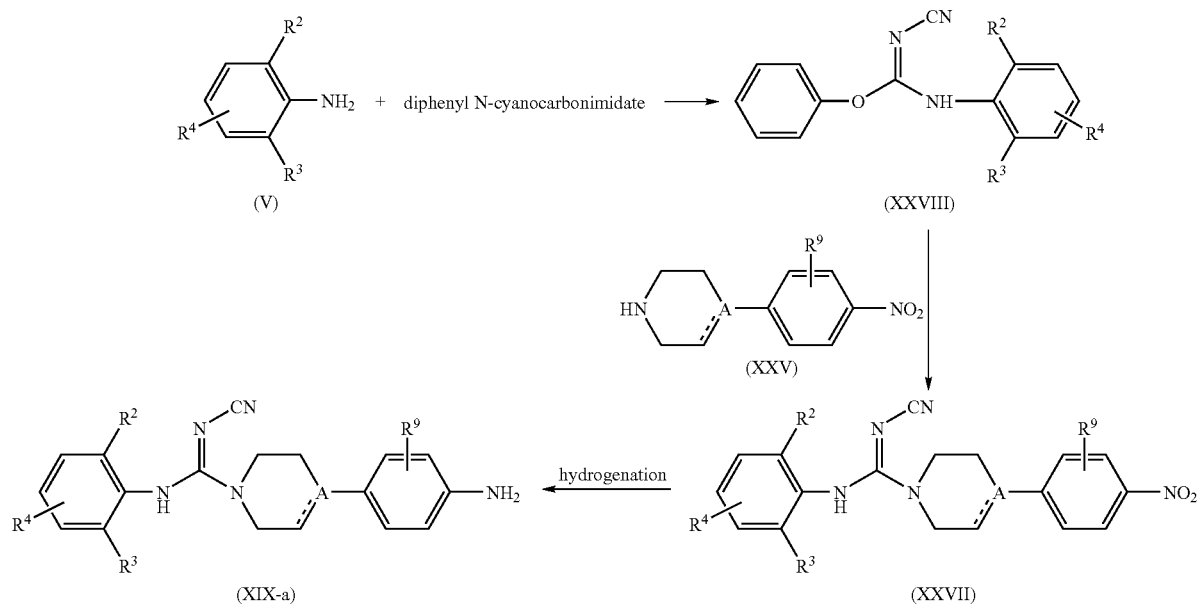

Intermediates of formula (V) wherein $R^4$ represents Het-$C_{1-4}$alkyl, wherein Het represents a monocyclic, saturated N containing heterocycle represented by formula (XXIX), said intermediate of formula (V) being represented by formula (V-a), can be prepared by reacting an intermediate of formula (XXIX) with an intermediate of formula (XXX) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate-(1-)3-oxide (HBTU), 1-[bis(dimethyl-amino)methylene]-5-chloro-1H-benzotriazo hum-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. The resulting intermediate of formula (XXXI) can then be reduced in a next step in the presence of a suitable reducing agent, such as for example borane, in the presence of a suitable solvent, such as for example tetrahydrofuran, to an intermediate of formula (V-a).

-continued

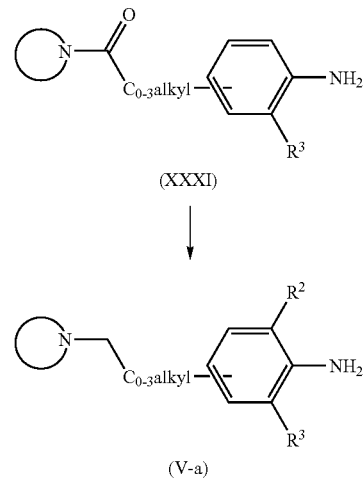

Intermediates of formula (V-a) can also be prepared by reacting an intermediate of formula (XXIX) with an intermediate of formula (XXXII) wherein $W_4$ represents a suitable leaving group, such as for example halo, e.g. chloro and the like, in the presence of a suitable solvent, such as for example acetonitrile, resulting in an intermediate of formula (V'-a).

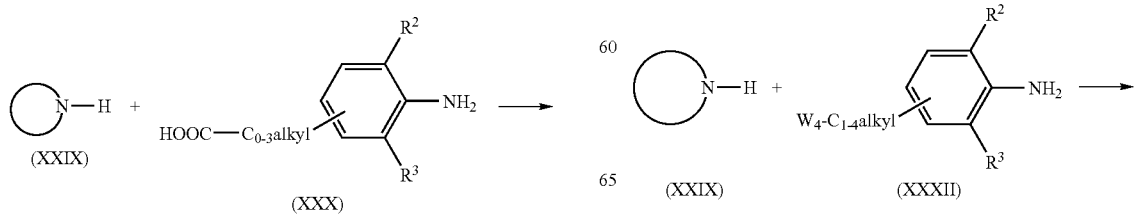

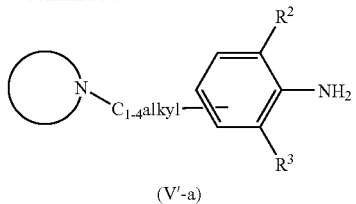

(V'-a)

Intermediates of formula (XXI) can be prepared by reacting an intermediate of formula (XIX) with an intermediate of formula (XXXIII) wherein $W_7$ represents a suitable leaving group, such as for example halo, e.g. chloro, bromo and the like, in the presence of a suitable base, such as for example N,N-diethyl-ethanamine, N,N-diisopropyl-ethanamine and a suitable solvent, such as for example dichloromethane or N,N-dimethylformamide.

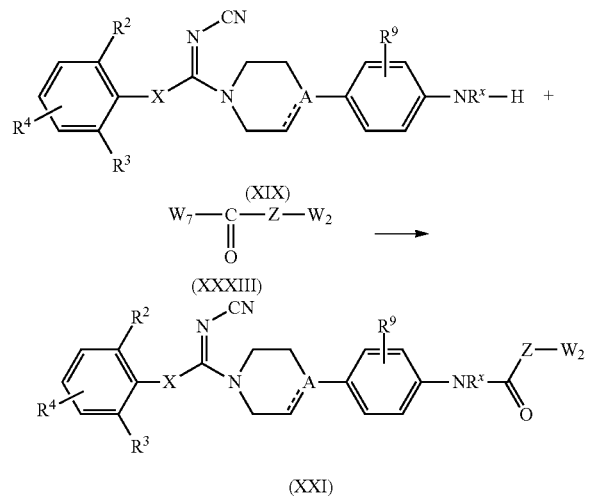

Pharmacological Part

As already indicated above, the present invention relates to the use of a DGAT inhibitor, in particular a DGAT1 inhibitor, to elevate levels of one or more satiety hormones, in particular GLP-1 levels. The present invention also relates to the use of a DGAT inhibitor, in particular a DGAT1 inhibitor, for the manufacture of a medicament for the prevention or the treatment, in particular for the treatment, of a disease which can benefit from an elevated level of one or more satiety hormones, in particular a disease which can benefit from an elevated GLP-1 level. In particular, GLP-1 levels are elevated in plasma or in portal blood, more in particular in plasma. By elevated GLP-1 levels, e.g. elevated GLP-1 plasma level or an elevated GLP-1 level in portal blood, it is meant that the GLP-1 level of a subject having taken a DGAT1 inhibitor is elevated or increased compared to the subject under the same conditions but not having taken the DGAT1 inhibitor. In particular GLP-1 levels are elevated in fasting conditions or postprandial, more in particular postprandial.

Therapeutic uses for a compound which elevates GLP-1 level include, but are not limited to, improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, hemorrhage, cerebrovascular accident, ADD, and neuropsychiatric syndromes; converting liver stem/progenitor cells into functional pancreatic cells; preventing beta-cell deterioration and stimulation of beta-cell proliferation; treating pancreatitis; treating obesity; suppressing appetite and inducing satiety; treating irritable bowel syndrome or inflammatory bowel disease such as Crohn's disease and ulcerative colitis; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction, e.g., with abnormal left ventricular ejection fraction; inhibiting antro-duodenal motility, e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS); modulating triglyceride levels and treating dyslipidemia; treating organ tissue injury (e.g. brain tissue injury) caused by reperfusion of blood flow following ischemia; improving the function of ischemic and reperfused brain tissue; treating coronary heart disease risk factor (CHDRF) syndrome. Further diseases which can benefit from an elevated GLP-1 level, include, but are not limited to, ischemic myocardial stunning; ishemic/reperfusion injury; acute myocardial infarction; left ventricular dysfunction; vascular disease; neuropathy, including periphere sensoric neuropathy associated with type II diabetes; bone-related disorders, including osteoporosis, obesity, diabetes. Because of the effect on GLP-1, the DGAT inhibitors can also be used to provide cardioprotection.

References supporting the above indications include Experimental Neurology, Vol. 203(2), pp 293-301 (2007); U.S. Pat. No. 7,186,683; J. Pharm. Exp. Ther. vol. 312, No. 1, pp 303-308 (2005); Diabetes, vol. 54, pp 146-151 (2005); US2007/0021339, which are incorporated herein by reference.

In view of the DGAT inhibitory activity, in particular the DGAT1 inhibitory activity, the present compounds of formula (I), their N-oxide forms, their pharmaceutically acceptable salts or their solvates, can be used as a medicine. In particular, the present invention relates to a compound of formula (I), a N-oxide form thereof, a pharmaceutically acceptable salt thereof or a solvate thereof for use as a medicine, in particular for use as a medicine for the prevention or the treatment of a disease which can benefit from an elevated GLP-1 level. In particular, the present invention also relates to the use of a compound of formula (I) for the manufacture of a medicament for the prevention or the treatment of a disease which can benefit from an elevated GLP-1 level, such as the diseases and disorders mentioned above.

In view of the above-described utility for a DGAT inhibitor, in particular a DGAT1 inhibitor, there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a DGAT inhibitor, in particular a DGAT1 inhibitor, to a warm-blooded mammal, including a human.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a compound of formula (I), a N-oxide form thereof, a pharmaceutically acceptable salt thereof or a solvate thereof, to a warm-blooded mammal, including a human.

In view of the DGAT inhibitory activity, in particular the DGAT1 inhibitory activity, the present invention also relates to a compound of formula (I), a N-oxide form thereof, a pharmaceutically acceptable salt thereof or a solvate thereof for use as a medicine, in particular for use as a medicine for the prevention or the treatment of a diseases which can benefit from inhibition of DGAT, in particular DGAT1. The invention also relates to the use of a compound of formula (I), a N-oxide form thereof, a pharmaceutically acceptable salt thereof or a solvate thereof, for the manufacture of a medicament for the prevention or the treatment of a disease or disorder which can benefit from inhibition of DGAT, in particular DGAT1. Diseases or disorders which can benefit from inhibition of DGAT, in particular DGAT1 include, but are not limited to metabolic disorders, such as obesity and obesity related disorders (including peripheral vascular disease, cardiac failure, myocardial ischaemia, cerebral ischaemia, cardiac myopathies), diabetes, in particular type II diabetes mellitus, and complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia and nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; and other diseases and conditions that are sensitive or responsive to modulation, in particular inhibition, of DGAT function, in particular DGAT1 function.

Particular diseases or disorders which can benefit from inhibition of DGAT, in particular DGAT1, are selected from obesity, hypercholesterolemia, hyperlipidemia, dyslipidemia, mixed dyslipidemia, hypertriglyceridemia, fatty liver, nonalcoholic fatty liver disease, liver fibrosis, non-alcoholic steatohepatitis and diabetes, in particular type II diabetes.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from inhibition of DGAT, in particular a method of treating a warm-blooded mammal, including a human, suffering from a disease which can benefit from inhibition of DGAT. Said methods comprise the administration of an effective amount of a compound of formula (I), a N-oxide form thereof, a pharmaceutically acceptable salt thereof or a solvate thereof, to a warm-blooded mammal, including a human.

The present invention also provides compositions for preventing or treating a disease which can benefit from an elevated GLP-1 level or which can benefit from inhibition of DGAT, in particular DGAT1, in particular for treating a disease which can benefit from elevated GLP-1 levels or which can benefit from inhibition of DGAT, in particular DGAT1. Said compositions comprise a therapeutically effective amount of a compound of formula (I), a N-oxide form thereof, a pharmaceutically acceptable salt thereof or a solvate thereof, and a pharmaceutically acceptable carrier.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

In view of the above described effects of DGAT inhibitors and/or the effect on GLP-1 levels by DGAT inhibitors, the present invention also relates to a) a combination of a DGAT inhibitor, in particular a DGAT1 inhibitor, more in particular a compound of formula (I), a N-oxide form thereof, a pharmaceutically acceptable salt thereof or a solvate thereof, and a dipeptidyl peptidase-4 inhibitor (DPP-4 inhibitor).

DPP-4 is a membrane-spanning cell surface aminopeptidase widely expressed in many tissues, such as liver, lung, kidney, intestinal brush-border membranes, lymphocytes, endothelial cells. DPP-4 cleaves peptides with a proline or alanine residue in the second aminoterminal position. Many gastro-intestinal hormones are substrates for DPP-4, among them GLP-1. A DPP-4 inhibitor thus inhibits cleavage of GLP-1 and hence provides for an increase in the level of GLP-1. Therefore, a combination as indicated above can be used to combine the activity of the DGAT inhibitor and the DPP4 inhibitor in order to elevate GLP-1 levels. By administering a DGAT inhibitor, in particular a DGAT1 inhibitor, more in particular a compound of formula (I), a N-oxide thereof, a pharmaceutically acceptable salt thereof or a solvate thereof, with a DPP4 inhibitor, different mechanisms may be targeted in order to achieve elevated levels of GLP-1. In this way, the use of such a combination may reduce the dosage of the DGAT inhibitor and the DPP4 inhibitor required for a desired elevation in GLP-1 level as compared to when the DGAT inhibitor or the DPP4 inhibitor is administered as a monotherapy. Therefore, these combinations may reduce or eliminate side effects of monotherapy while not interfering with the GLP-1 level increasing activity.

Also, the combination of a DGAT inhibitor, in particular a DGAT1 inhibitor, more in particular a compound of formula (I), a N-oxide form thereof, a pharmaceutically acceptable salt thereof or a solvate thereof, and a DPP4 inhibitor can be used as a medicine. The present invention also relates to a product comprising (a) a DGAT inhibitor, in particular a DGAT1 inhibitor, more in particular a compound of formula (I), a N-oxide form thereof, a pharmaceutically acceptable salt thereof or a solvate thereof, and (b) a DPP4 inhibitor, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers. Said DPP4 inhibitor which may be combined with a DGAT inhibitor according to the present invention, in particular a DGAT1 inhibitor, may be a known DPP4 inhibitor such as for example sitagliptin, vildagliptin, and saxagliptin.

b) a combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue. Said GLP-1 analogue can be considered as an agonist at the GLP-1 receptor.

Also, the combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a GLP-1 analogue, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers.

Said GLP-1 analogue which may be combined with a DGAT inhibitor according to the present invention may be a known GLP-1 analogue such as for example exenatide, exenatide LAR or liraglutide.

c) a combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-diabeticum, as a combined preparation for simultaneous, separate or sequential use in the treatment of a disease which can benefit from an elevated level of GLP-1 or DGAT inhibition, such as for example diabetes, in particular type II diabetes. The different drugs of such a combination or product may be combined in a single preparation together with pharmaceutically acceptable carriers or they may each be present in a separate preparation together with pharmaceutically acceptable carriers. Said anti-diabeticum which may be combined with a DGAT inhibitor according to the present invention may be a known anti-diabeticum such as for example metformin, glibenclamide, rosiglitazon, pioglitazon, repaglinide, glimepiride, acarbose, glicazide, glipizide, nateglinide, tolbutamide, a protein tyrosine phosphatase 1 inhibitor, or a 11-beta-hydroxysteroid dehydrogenase inhibitor.

d) a combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor. Phosphodiesterase (PDE) inhibitors, in particular PDE10A or PDE11A inhibitors, are known to be insulin secretagogues, and to enhance the signalling of GLP-1 by inhibition of the hydrolysis of cAMP.

Also, the combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a phosphodiesterase (PDE) inhibitor, in particular a PDE10A or PDE11A inhibitor, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said phosphodiesterase (PDE) inhibitor, in particular a PDE10A or PDE11A inhibitor, which may be combined with a DGAT inhibitor according to the present invention may be a known PDE inhibitor such as for example papaverine, PQ-10, dipyridamole, ibudilast or tadalafil.

e) a combination of a DGAT inhibitor, in particular a DGAT1 inhibitor, more in particular a compound of formula (I), a N-oxide form thereof, a pharmaceutically acceptable salt thereof or a solvate thereof, and an appetite suppressant.

Also, the combination of a DGAT inhibitor, in particular a DGAT1 inhibitor, more in particular a compound of formula (I), a N-oxide form thereof, a pharmaceutically acceptable salt thereof or a solvate thereof, and an appetite suppressant can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an appetite suppressant, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said appetite suppressants, which may be combined with a DGAT inhibitor according to the present invention may be a known appetite suppressant such as for example sibutramine and phentermine.

f) a combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action such as for example a CB1 antagonist or inverse agonists.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-obesity drug with a CNS (central nervous system) mode of action, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-obesity drugs with a CNS (central nervous system) mode of action, which may be combined with a DGAT inhibitor according to the present invention may be a known a anti-obesity drug such as for example Rimonabant, orlistat, SLV-319, or MK-0364.

g) a combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug such as for example 3-hydroxy-3-methyl-glutaryl coenzyme A (HMG-CoA) reductase inhibitors, squalene synthase inhibitors, FXR (farnesoid X receptor) and LXR (liver X receptor) ligands, cholestyramine, fibrates, nicotinic acid and aspirin.

Also, the combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an hypolipidemic drug, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said hypolipidemic drug which may be combined with a DGAT inhibitor according to the present invention may be a known hypolipidemic drug such as for example lovastatin, pravastatin, simvastatin, pravastatin, cerivastatin, mevastatin, velostatin, fluvastatin, dalvastatin, atorvastatin, rosuvastatin and rivastatin.

h) a combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate.

Also, the combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an agonist of peroxisome proliferator-activator receptor such as for example fenofibrate, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers.

i) a combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent.

Also, the combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an antihypertensive agent, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-hypertensive agent which may be combined with a DGAT inhibitor according to the present invention may be a known anti-hypertensive agent, e g loop diuretics such as ethacrynic acid, furosemide and torsemide, angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The following examples are intended to illustrate the present invention.

EXPERIMENTAL PART

Hereinafter "DMF" means N,N-dimethylformamide, "DIPE" means diisopropyl ether, "DCM" means dichloromethane, "THF" means tetrahydrofuran, "EDCI" means N-(ethylcarbonimidoyl)-N,N-dimethyl-1,3-propanediamine monohydrochloride, 'HOBT' means 1-hydroxy-M-benzotriazole, "EtOAc" means ethyl acetate, "Et$_2$O" means diethyl ether, "p.a." means pro analysis and "DMSO" means dimethylsulfoxide.

A number of compounds were purified by reversed phase high-performance liquid chromatography using the method below.

HPLC Method A

The product was purified by high-performance liquid chromatography (Shandon Hyperprep® C18 BDS (Base Deactivated Silica) 8 μm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN).

A. Preparation of the Intermediate Compounds

Example A1 a) Preparation of Intermediate 1

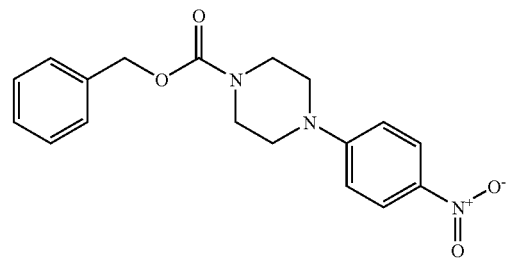 [SMILES: O=C(OCc1ccccc1)N1CCN(c2ccc([N+](=O)[O-])cc2)CC1]

In a mechanically stirred flask under N$_2$ atmosphere 1-(4-nitrophenyl)piperazine (100 g; 483 mmol) and NaHCO$_3$ (44.61 g, 1.1 equiv) in DCM (600 ml) were cooled on an ice-water bath at 8° C. Phenylmethyl carbonochloridic acid ester (86.49 g, 1.05 equiv) dissolved in 120 ml DCM was added dropwise during 2 hours while maintaining the temperature below 15° C. After 15 hours stirring at room temperature another 8.15 g of NaHCO$_3$ (0.2 equiv) and a solution of 16.50 g phenylmethyl carbonochloridic acid ester (0.2 equiv) in 50 ml DCM were added dropwise at room temperature. 5 hours later acetonitrile was added and further stirred for 18 hours. Then 500 ml water was added and the reaction mixture was stirred for another hour before separating the phases. The aqueous layer was extracted again with DCM. After drying (MgSO$_4$), and evaporation of the organic phase, 225.33 g orange powder was recuperated. It was stirred and resuspended in DIPE for a couple of hours, filtered and dried in vacuo at 50° C. Yield 158.58 g of intermediate 1 (96%) (152-156° C.).

b) Preparation of Intermediate 2

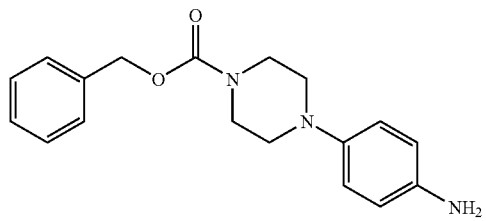 [SMILES: Nc1ccc(N2CCN(C(=O)OCc3ccccc3)CC2)cc1]

Intermediate 1 (80 g; 234 mmol) was hydrogenated overnight at room temperature with 5 g Pt/C$_5$% as a catalyst in the presence of 3 ml of a thiophene solution, 250 ml methanol and 250 ml THF. After uptake of hydrogen, the catalyst was filtered off and the filtrate was evaporated. The residue was triturated in hot DIPE, cooled to room temperature, filtered and dried overnight in vacuo at 50° C. Yield: 62.8 g of intermediate 2; mp. 70-76.5° C.

c) Preparation of Intermediate 3

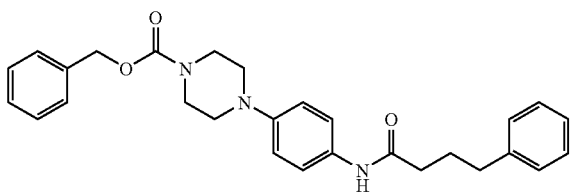 [SMILES: O=C(CCCc1ccccc1)Nc1ccc(N2CCN(C(=O)OCc3ccccc3)CC2)cc1]

Benzenebutanoic acid (0.1670 mol) in thionyl chloride (1.7 mol) was stirred overnight at room temperature. The solution was evaporated and coevaporated twice with toluene. This residue was dissolved in 100 ml of acetonitrile and added dropwise to a suspension of intermediate 2 and NaHCO$_3$ in 500 ml acetonitrile which was cooled on a water bath for 15 minutes. The mixture was treated with 2.5 l water and stirred for 2 hours. The precipitate was recuperated, washed with water and recrystallized from 400 ml boiling ethanol. Yield: 64.2 g of intermediate 3 (88%)

d) Preparation of Intermediate 4

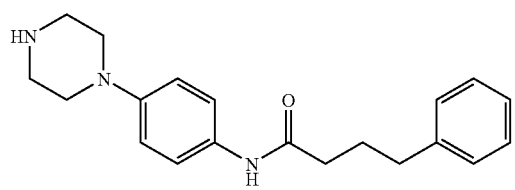 [SMILES: O=C(CCCc1ccccc1)Nc1ccc(N2CCNCC2)cc1]

A solution of intermediate 3 (0.095 mol) in methanol (500 ml) was hydrogenated in a Parr apparatus (8 pounds pressure) with Pd/C 10% (5 g) as a catalyst. After uptake of hydrogen (1 equiv), the catalyst was filtered off, the filtrate was evaporated and coevaporated with toluene, yielding 35.7 g of intermediate 4 (99%).

e) Preparation of Intermediate 5

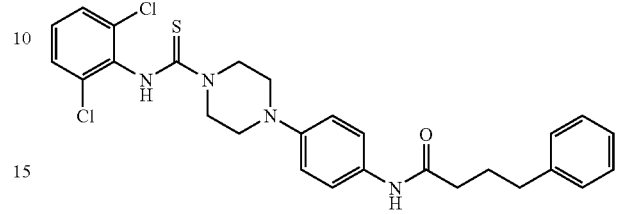

Intermediate 4 (0.0025 mol) was added to a stirring solution of 1,3-dichloro-2-isothiocyanatobenzene (0.00275 mol) in THF (15 ml). The reaction mixture was stirred for 18 hours at room temperature. The precipitate was filtered off, washed with THF (3 x), with diethyl ether (3×), and dried (vacuum, 60° C.). Yield: 0.924 g of intermediate 5 (70%).

Example A2 a-1) Preparation Of Intermediate 6

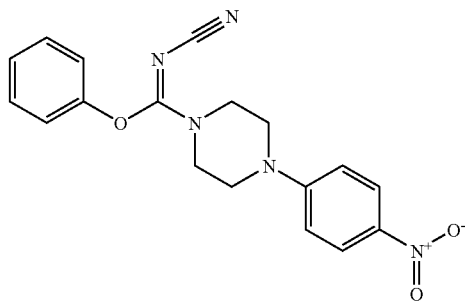 [SMILES: N#C/N=C(/Oc1ccccc1)N1CCN(c2ccc([N+](=O)[O-])cc2)CC1]

A mixture of 1-(4-nitrophenyl)piperazine (50 g, 0.24 mol), diphenyl N-cyanocarbonimidate (57.2 g, 0.24 mol) and THF (dry) was stirred for 20 hours at 50° C. The product was precipitated. The mixture was cooled and the product was filtered off, washed (DIPE) and dried. Yield: 80.5 g of intermediate 6.

a-2) Preparation Of Intermediate 7

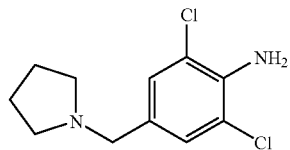 [SMILES: Nc1c(Cl)cc(CN2CCCC2)cc1Cl]

A mixture of pyrrolidine (22.2 ml, 0.27 mol) and acetonitrile (150 ml) was stirred and cooled on an ice bath. 2,6-Dichloro-4-(chloromethyl)-benzenamine hydrochloride (6.7 g, 0.027 mol) was added portionwise over 30 minutes while cooling with ice. After the addition, the mixture was stirred on an ice bath for 10 minutes and subsequently at room temperature for 1 hour. The solvent was evaporated at 50° C. The residue was stirred in water, treated with Na$_2$CO$_3$, and was then extracted with DCM. The layers were separated. The organic layer was dried, filtered and the solvent was evaporated. Yield: 6.5 g of the crude intermediate. Part of this crude product (3.25 g) was filtered over silica gel using a mixture of DCM and CH$_3$OH (95/5) as eluent. The desired fractions were collected to yield 2.1 g of intermediate 7.

b) Preparation of Intermediate 8

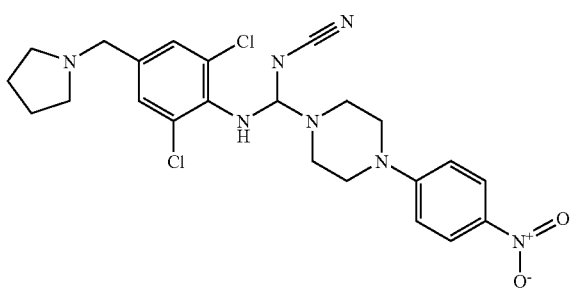 [SMILES: N#CNC(Nc1c(Cl)cc(CN2CCCC2)cc1Cl)N1CCN(c2ccc([N+](=O)[O-])cc2)CC1]

A mixture of intermediate 7 (2.45 g, 0.010 mol) and DMF (25 ml) was stirred at room temperature. NaH (0.800 g, 0.020 mol; 60%) was added portionwise over 15 minutes. Subsequently, the mixture was stirred at 50° C. for 30 minutes. The mixture was cooled at room temperature. Intermediate 6 (3.51 g, 0.010 mol) was added. The mixture was stirred overnight at room temperature. The solvent was evaporated. The residue was stirred in water. This mixture was first treated with CH$_3$COOH till pH 5-6 and then with NaHCO$_3$ till pH 8. Then the mixture was extracted with DCM. An undissolved solid was filtered off and then the layers of the filtrate were separated. The organic layer was dried, filtered and the solvent was evaporated. The residue was purified by HPLC method A. The pure fractions were collected and the solvent was partially evaporated (till about 200 ml). The product was precipitated, filtered off and dried. Yield: 2.13 g of intermediate 8.

c) Preparation of Intermediate 9

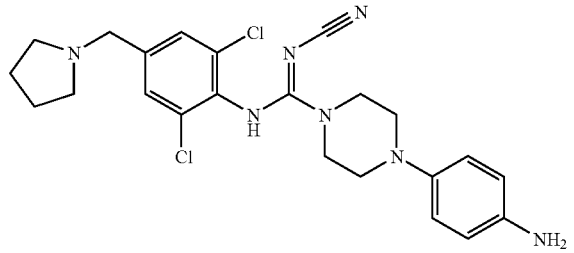 [SMILES: N#C/N=C(/Nc1c(Cl)cc(CN2CCCC2)cc1Cl)N1CCN(c2ccc(N)cc2)CC1]

A mixture of intermediate 8 (1.2 g, 0.0024 mol), a thiophene solution (3 ml; 4% in DIPE) and THF (120 ml) was hydrogenated over Pt/C (0.4 g; 5%) at room temperature under normal pressure. After H$_2$ (0.0072 mol) was taken up, the catalyst was filtered off and the filtrate was evaporated. The crude residue was used as such in the next reaction step. Yield: 1.13 g of intermediate 9.

Example A3 a) Preparation of Intermediate 10

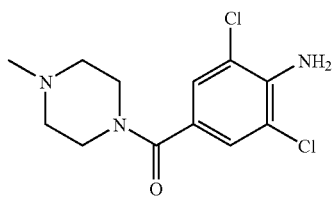 [SMILES: CN1CCN(C(=O)c2cc(Cl)c(N)c(Cl)c2)CC1]

A mixture of 4-amino-3,5-dichlorobenzoic acid (20.6 g, 0.100 mol), EDCI (21.1 g, 0.110 mol), HOBT (14.9 g) and DMF (200 ml) was stirred for 15 minutes at room temperature. Then 1-methyl-piperazine (11 g, 0.110 mol) was added and the mixture was stirred for 3 hours. The product was precipitated. The solid was filtered off, washed with DIPE and dried. Yield: 5.9 g of intermediate 10. The filtrate was evaporated. The residue was stirred in DMF. The product was filtered off, washed with DIPE and dried to yield a second amount (10 g) of intermediate 10.

b) Preparation of Intermediate 11

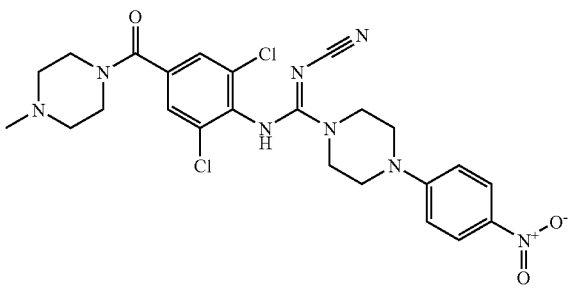 [SMILES: CN1CCN(C(=O)c2cc(Cl)c(N/C(=N/C#N)N3CCN(c4ccc([N+](=O)[O-])cc4)CC3)c(Cl)c2)CC1]

A mixture of intermediate 10 (3.9 g, 0.0135 mol) and DMF (30 ml) was stirred at room temperature. NaH (1.08 g, 0.027 mol; 60%) was added portionwise over 30 minutes. The mixture was stirred for 30 minutes. Intermediate 6 (4.75 g, 0.0135 mol) was added. The mixture was stirred at room temperature for 18 hours. The solvent was evaporated. The residue was stirred in water and extracted with DCM. The layers were separated. Since the water layer still contained the major part of the desired intermediate, the water layer was first treated with CH$_3$COOH till pH 5 and then with NaHCO$_3$ until pH 8 and was subsequently extracted with DCM. An undissolved solid was filtered off and the layers were separated. The organic layer was dried, filtered and the solvent was evaporated. The residue (solid) was dried. Yield: 3.4 g of intermediate 11.

c) Preparation of Intermediate 12

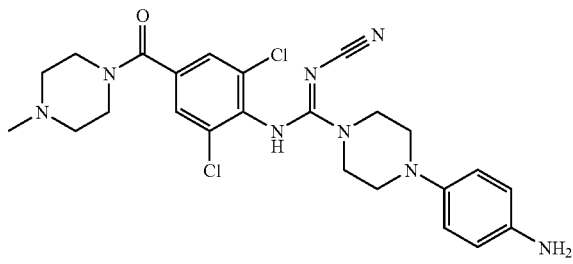 [SMILES: CN1CCN(C(=O)c2cc(Cl)c(N/C(=N/C#N)N3CCN(c4ccc(N)cc4)CC3)c(Cl)c2)CC1]

A mixture of intermediate 11 (3.4 g, 0.0062 mol), a thiophene solution (4% in DIPE) and CH₃OH (q.s.) was hydrogenated at room temperature under normal pressure with Pt/C (1 g; 5%) as the catalyst. After 3 equivalents of H$_2$ were taken up, the catalyst was filtered off. The filtrate was evaporated to yield 3.2 g of intermediate 12 as a crude residue.

Example A4 a) Preparation of Intermediate 13

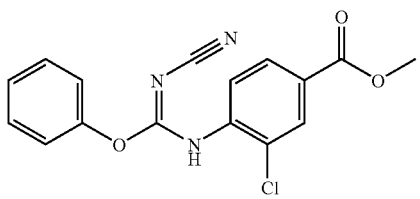 [SMILES: COC(=O)c1ccc(N/C(=N\C#N)Oc2ccccc2)c(Cl)c1]

A solution of diphenyl N-cyanocarbonimidate (4.6 g, 0.0194 mol), 4-amino-3-chlorobenzoic acid methyl ester (3.6 g, 0.0194 mol) and pyridine (5 ml; p.a. dried on molecular sieves) was stirred for 45 minutes at 60° C. An extra amount of pyridine (5 ml) was added and the reaction mixture was continued stirring for 2 hours at 60° C. The crude mixture (containing intermediate 13) was used as such in the next reaction step.

b) Preparation of Intermediate 14

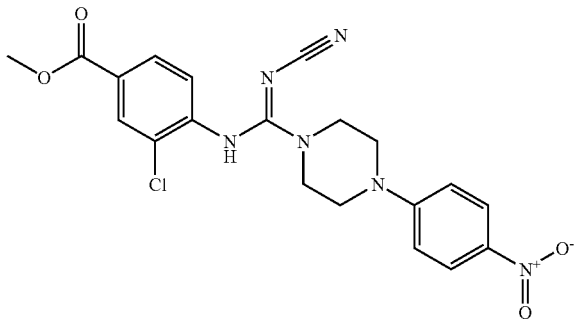 [SMILES: COC(=O)c1ccc(N/C(=N/C#N)N2CCN(c3ccc([N+](=O)[O-])cc3)CC2)c(Cl)c1]

1-(4-Nitrophenyl)piperazine (4.02 g, 0.0194 mol) was added to intermediate 13 (crude reaction mixture from previous reaction step; max. 0.0194 mol) in pyridine (10 ml; p.a. dried on molecular sieves). Subsequently more pyridine (5 ml) was added and the reaction mixture was heated to 100° C. The mixture was stirred at 100° C. for 20 minutes and was then allowed to reach room temperature. The mixture was left standing overnight. EtOAc (15 ml) was added and the mixture was stirred for 15 minutes. The precipitate was filtered off, washed (3× with EtOAc) and dried (50° C., in vacuo). Yield: 6.5 g of intermediate 14 (76%).

c) Preparation of Intermediate 15

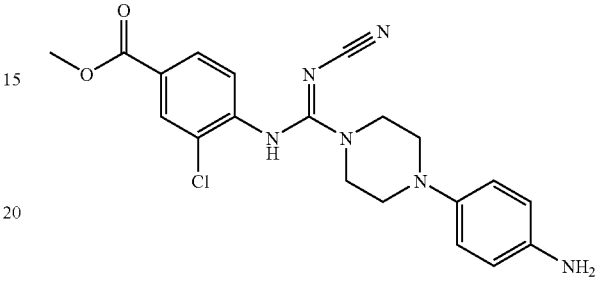

A solution of intermediate 14 (4.7 g, 0.0106 mol) in a thiophene solution (4% in DIPE) (2 ml) and CH₃OH (150 ml) was hydrogenated with Pt/C (1 g; 10%) as a catalyst. After H$_2$ (855 ml) was taken up, the catalyst was filtered off. The filtrate was evaporated and the residue was stirred in Et₂O (50 ml)/EtOAc (5 ml). The desired intermediate was filtered off, washed (2× with Et₂O) and dried (50° C., in vacuo). Yield: 3.81 g of intermediate 15 (87%).

B. Preparation of the Final Compounds

Example B1

Preparation of Compound 1

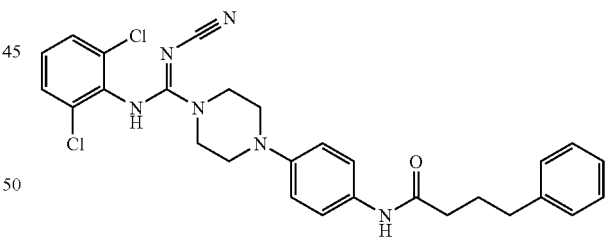

A mixture of intermediate 5 (0.000474 mol) and lead cyanamide (0.000566 mol) in DMF (4.5 ml) was stirred at 140° C. in a microwave oven. After one hour, more lead cyanamide (0.000566 mol) was added and the reaction mixture was heated for one hour at 140° C. in a microwave oven. The mixture was allowed to cool to room temperature and stood for one hour at room temperature, then filtered over dicalite. The filtrate's solvent was evaporated. The residue was purified by reversed-phase HPLC (HPLC method A). The product fractions were collected and the organic solvent was evaporated. The aqueous concentrate stood overnight. The precipitate was filtered off, washed with water (3×), and dried (vacuum, 50° C.). This fraction was dissolved in DCM/

CH$_3$OH, transferred into an appropriate vessel, then the solvent was evaporated again. Yield: 0.038 g of compound 1 (15%).

Example B2

Preparation of Compound 2

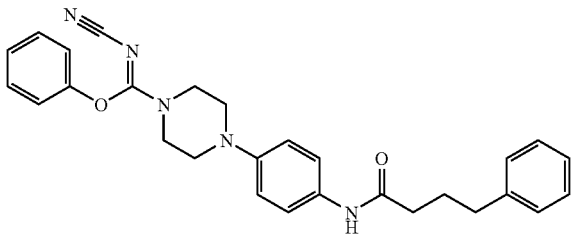 [SMILES: N#C/N=C(\Oc1ccccc1)N1CCN(c2ccc(NC(=O)CCCc3ccccc3)cc2)CC1]

A solution of intermediate 4 (0.003 mol) and cyanocarbonimidic acid diphenyl ester (0.0031 mol) in THF (15 ml) was stirred at 55° C. for 18 hours. The mixture was allowed to cool to room temperature, then poured out into water (50 ml). This mixture was extracted with DCM. The separated organic layer was dried (MgSO$_4$), filtered and the solvent was evaporated. The residue was stirred in ethanol, filtered off, washed with ethanol, then dried in vacuo at 50° C. Yield: 0.94 g of compound 2 (67%).

Example B3 a) Preparation of Compound 3

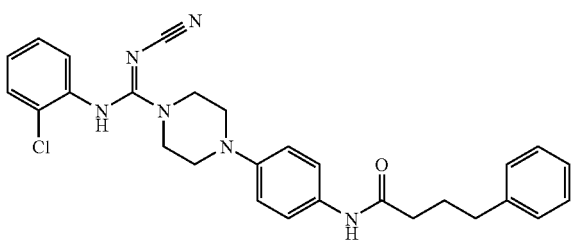 [SMILES: N#C/N=C(/Nc1ccccc1Cl)N1CCN(c2ccc(NC(=O)CCCc3ccccc3)cc2)CC1]

NaH, 60% in mineral oil (0.00137 mol) was added to a stirring solution of 1-amino-2-chlorobenzene (0.0047 mol) in 1,4-dioxane (1.5 ml), under N$_2$ atmosphere. The mixture was stirred for one hour. Compound 2 (0.000427 mol) was added. The resultant reaction mixture was stirred for 18 hours at room temperature. The reaction mixture was poured out into water (8 ml). This mixture was extracted with DCM. The separated organic layer was dried (MgSO$_4$), filtered and the filtrate was concentrated to ±1.5 ml volume. The desired compound precipitated out from the concentrate. The precipitate was filtered off, washed with 1,4-dioxane, with diethyl ether, then dried (vacuum, 50° C.). Yield: 0.131 of compound 3 (61%).

b) Preparation of Compound 4

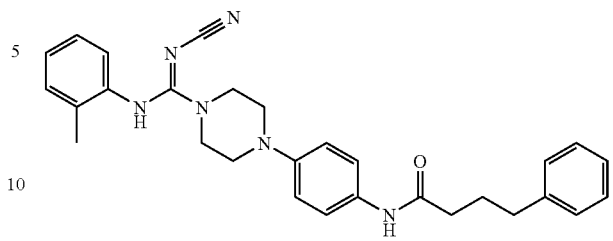

NaH, 60% in mineral oil (0.00137 mol) was added to a stirring solution of 1-amino-2-methylbenzene (0.5 ml) in 1,4-dioxane (1.5 ml), under N$_2$ atmosphere. The resultant mixture was stirred for 90 minutes. Compound 2 (0.000427 mol) was added. The resultant reaction mixture was stirred for 18 hours at room temperature. The solvent was evaporated. 1-Methyl-2-pyrrolidinone (2.5 ml) was added. The reaction mixture was stirred for 2.5 hours at 110° C. The reaction mixture was cooled, poured out into water (35 ml), then washed with diethyl ether. HOAc was added to the separated water layer until pH=1.5. This mixture was extracted with EtOAc. A lot of undissolved material remained in between the two layers. The biphasic mixture was filtered to get the biphasic filtrate which was separated (*) and the undissolved material which was dissolved in DCM/CH$_3$OH 95/5 (50 ml)+a half-saturated aqueous NaHCO$_3$ solution (25 ml). The organic layer of the DCM/CH$_3$OH 95/5 (50 ml)+a half-saturated aqueous NaHCO$_3$ solution mixture was separated, combined with the previous separated EtOAc layer (*), dried (MgSO$_4$), filtered and the solvent was evaporated. The residue was purified by reversed-phase HPLC (HPLC method A). The desired fractions were collected and the solvent was evaporated, then co-evaporated 4× with methanol. Yield: 0.013 g of compound 4 (6%).

c) Preparation of Compound 5

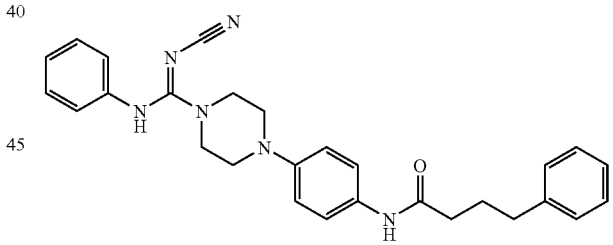

NaH, 60% in mineral oil (0.001 mol) was added to a stirring mixture of compound 2 (0.00032 mol) in aminobenzene (2 ml; p.a., dried over molecular sieves). The reaction mixture was stirred for 3 hours at room temperature. The reaction mixture was poured out into water (15 ml). This mixture was extracted with DCM. The separated organic layer was washed with water (4×), dried (MgSO$_4$), filtered and the solvent was evaporated. The residue was stirred in diethyl ether, then decanted (3×). The residue was purified over a Flash tube (eluent: DCM/CH$_3$OH 90/10). The product fractions were collected and the solvent was evaporated. The residue was stirred in DCM/CH$_3$OH 90/10, then filtered off and washed to remove the silica gel, and the filtrate's solvent was evaporated. The residue was purified by reversed-phase HPLC (HPLC method A). The product fractions were collected and the organic volatiles were evaporated. The precipitate was filtered off from the aqueous concentrate, was washed with water, and dried (vacuum, 60° C.). Yield: 0.017 g of compound 5 (11%).

Example B4

Preparation of Compound 6

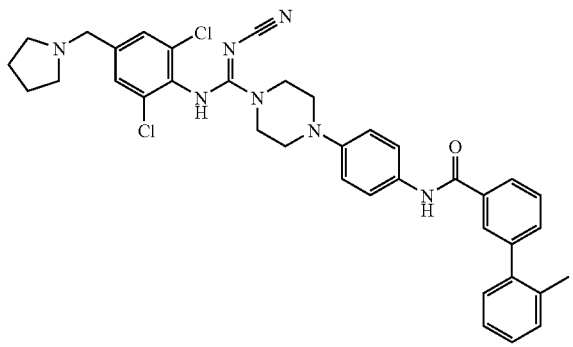 [SMILES: Cc1ccccc1-c1cccc(C(=O)Nc2ccc(N3CCN(/C(=N\C#N)Nc4c(Cl)cc(CN5CCCC5)cc4Cl)CC3)cc2)c1]

A mixture of intermediate 9 (1 g, 0.002 mol), 2'-methyl-[1,1'-biphenyl]-3-carboxylic acid (0.43 g, 0.002 mol), EDCI (0.38 g, 0.002 mol), 1-hydroxy-1H-benzotriazole hydrate (0.31 g, 0.002 mol), $Et_3N$ (0.28 ml, 0.002 mol) and DMF (10 ml) was stirred at room temperature for 18 hours. Then the solvent was evaporated. The residue was stirred in water and extracted with DCM. The organic layer was dried, filtered and the solvent was evaporated. The residue was purified over silica gel using a mixture of DCM and $CH_3OH$ (90/10) as eluent. The fractions containing the product were collected and the solvent was evaporated, yielding 1.1 g of residue. This residue was purified by HPLC method A. The pure fractions were collected and the solvent was evaporated. The residue was stirred in DIPE. The product was filtered off and dried. Yield: 0.638 g of compound 6.

Example B5

Preparation of Compound 7

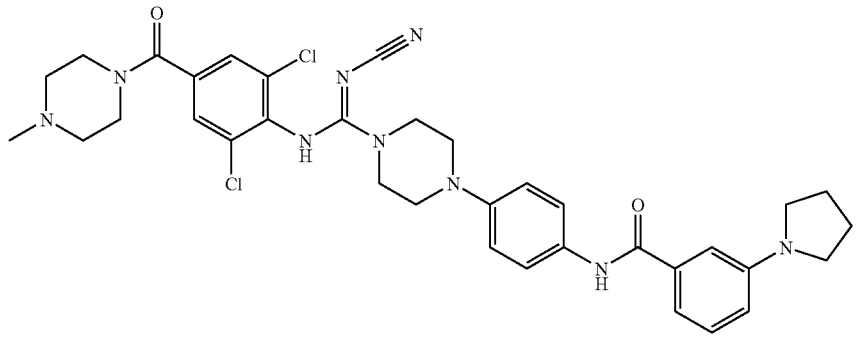 [SMILES: CN1CCN(C(=O)c2cc(Cl)c(N/C(=N/C#N)N3CCN(c4ccc(NC(=O)c5cccc(N6CCCC6)c5)cc4)CC3)c(Cl)c2)CC1]

A mixture of intermediate 12 (1.03 g, 0.002 mol), 3-(1-pyrrolidinyl)benzoic acid (0.38 g, 0.002 mol), EDCI (0.42 g, 0.0022 mol), 1-hydroxy-1H-benzotriazole hydrate (0.34 g, 0.0022 mol), $Et_3N$ (0.0022 mol) and DMF (10 ml) was stirred at room temperature for 18 hours. Then the solvent was evaporated. The residue was stirred in water and extracted with $DCM/CH_3OH$ 90/10. The organic layer was dried, filtered and the solvent was evaporated. This residue was purified by HPLC method A. The pure fractions were collected and the solvent was evaporated. The residue was dried. Yield: 0.428 g of compound 7.

Example B6

Preparation of Compound 9

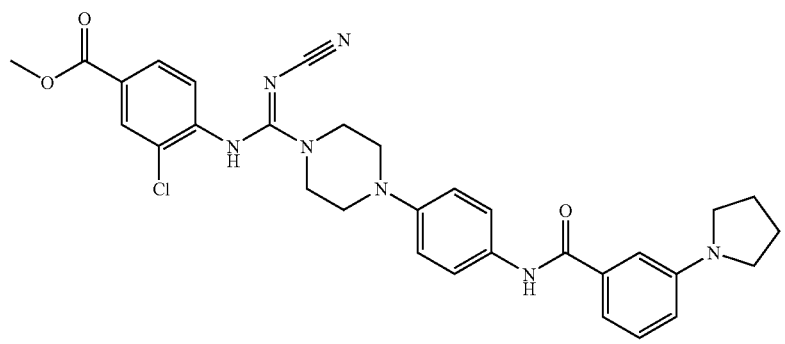 [SMILES: COC(=O)c1ccc(N/C(=N/C#N)N2CCN(c3ccc(NC(=O)c4cccc(N5CCCC5)c4)cc3)CC2)c(Cl)c1]

Phosphorocyanidic acid diethyl ester (0.112 ml, 0.000752 mol) was added to a stirring mixture of intermediate 15 (0.27 g, 0.000654 mol), 3-(1-pyrrolidinyl)benzoic acid (0.138 g, 0.000719 mol), Et₃N (0.11 ml, 1.2 equivalent) and THF (10 ml; p.a. dried on molecular sieves). The reaction mixture was stirred for 24 hours at room temperature under N₂ flow and was then left standing for 72 hours. Subsequently, the product was filtered off, washed (2× with THF and 2× with Et₂O) and dried (50° C., vacuum). Yield: 0.04 g of compound 9 (10%).

The below compounds of formula (I) according to the present invention were prepared by analogy to one of the above Example Nr.

Compound 8

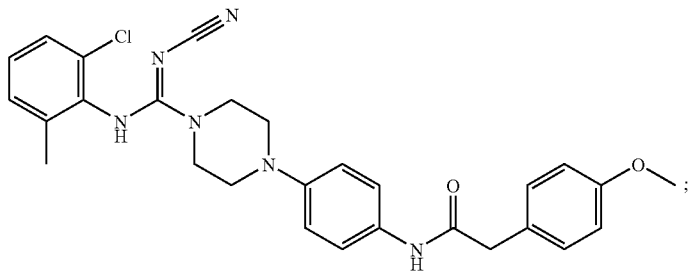

B3.b

Compound 10

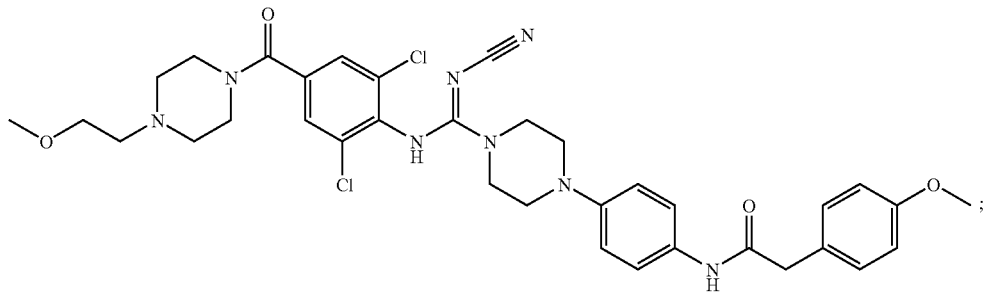

B5

Compound 11

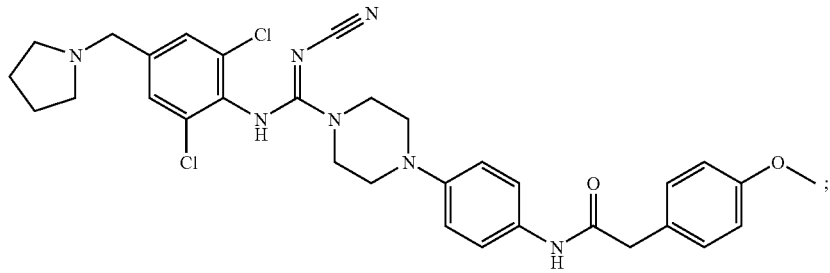

B4

Compound 12

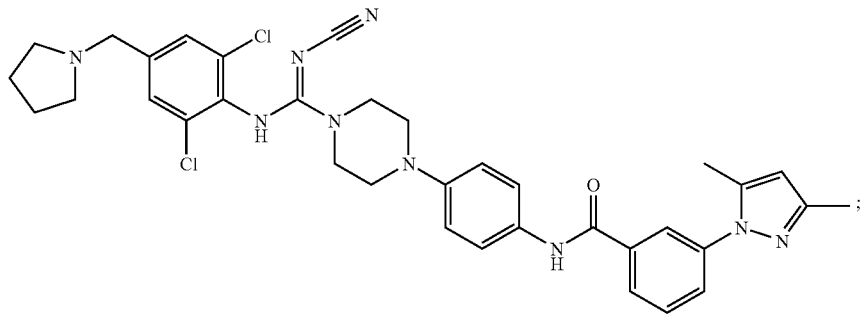

B4

-continued
Compound 13
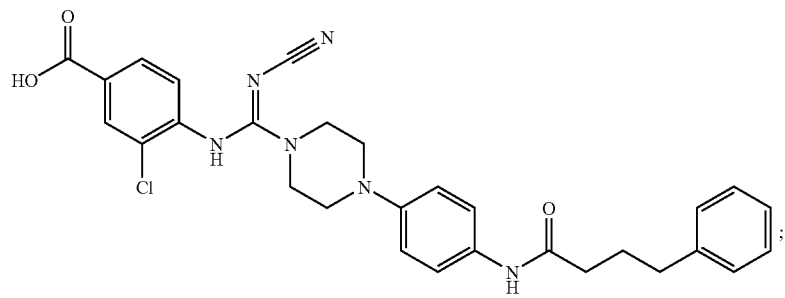
B6
Compound 14
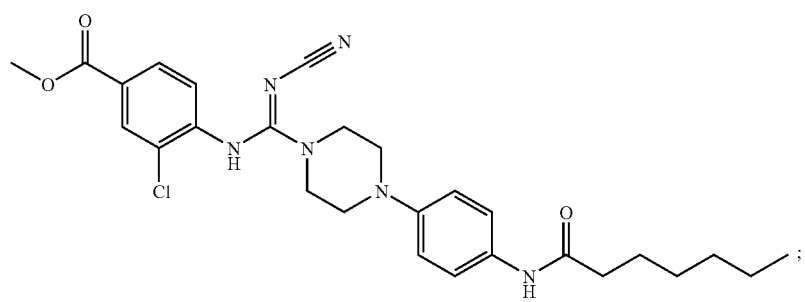
B6
Compound 15
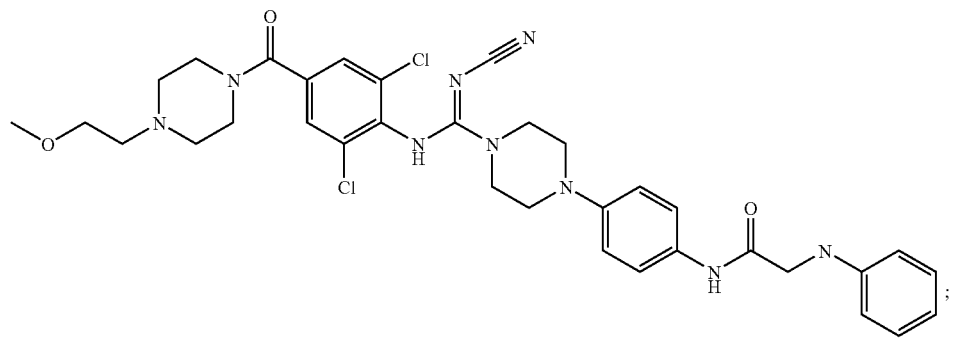
B5
Compound 16
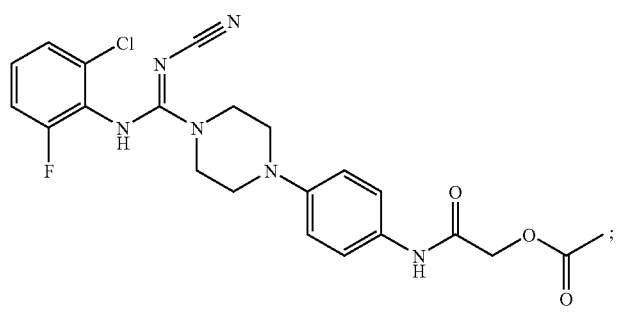
B3.b -continued

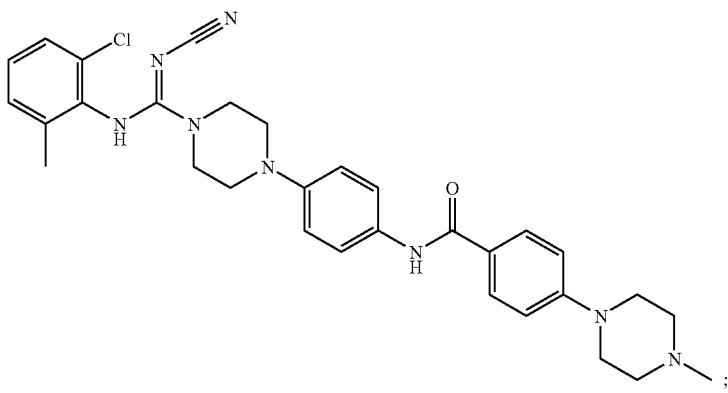

B3.b

Compound 17

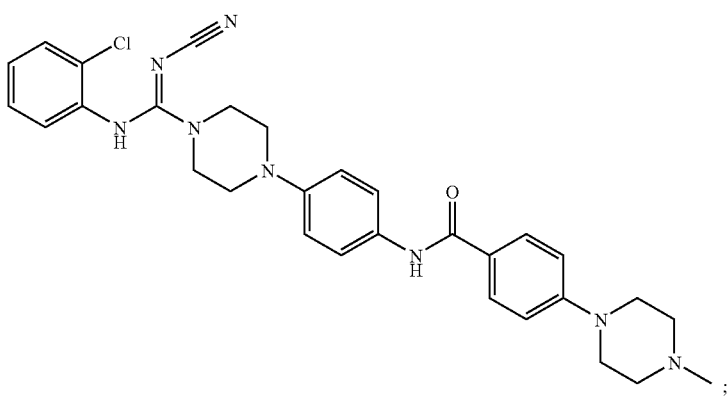

B3.a

Compound 18

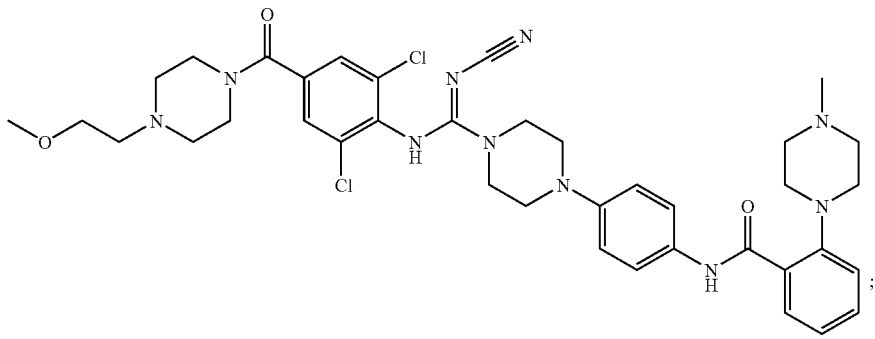

B5

Compound 19

C. Analytical Part

LCMS

For LCMS-characterization of the compounds of the present invention, the following methods were used.

General Procedure A

The HPLC measurement was performed using an Alliance HT 2790 (Waters) system comprising a quaternary pump with degasser, an autosampler, a column oven, a diode-array detector (DAD) and a column as specified in the respective methods below. Flow from the column was split to a MS detector. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS Method 1

In addition to the general procedure A: (Column heater was set at 40° C.) Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 was used. Cone voltage was 10 V for positive ionization mode and 20 V for negative ionization mode.

LCMS Method 2

In addition to the general procedure A: (Column heater was set at 60° C.) Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS Method 3

In addition to the general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in H$_2$O/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./minute. Maximum temperature was 400° C. Values are peak values.

TABLE 1

Analytical data

| Co. No. | R$_t$ | (MH)$^+$ | LCMS Method | m.p. (° C.) |
|---|---|---|---|---|
| 1 | 5.17 | 535 | 2 | n.d. |
| 3 | 5.78 | 501 | 1 | n.d. |
| 4 | 5.19 | 481 | 2 | n.d. |
| 2 | 5.98 | 468 | 1 | n.d. |
| 5 | 5.72 | 467 | 1 | n.d. |
| 6 | 5.95 | 666 | 2 | 217.1 |
| 7 | 5.48 | 688 | 2 | n.d. |
| 8 | 4.12 | 517 | 1 | 206.9 |
| 9 | 5.92 | 586 | 1 | 220.3 |
| 10 | 0.92 | 707 | 3 | 205.3 |
| 11 | 4.87 | 620 | 2 | 222.4 |
| 12 | 5.35 | 670 | 2 | n.d. |
| 13 | 4.26 | 545 | 2 | 208.7 |
| 14 | 5.56 | 523 | 2 | 191.8 |
| 15 | 4.97 | 692 | 1 | 211.9 |
| 16 | 3.93 | 473 | 2 | 209.0 |
| 17 | 4.83 | 571 | 1 | 285.1 |
| 18 | 0.83 | 557 | 3 | 244.2 |
| 19 | 0.72 | 761 | 3 | 254.2 |

(Co. No means compound number; R$_t$ means retention time in minutes; (MH)$^+$ means the protonated mass of the compound; LCMS Method refers to the method used for LCMS; m.p. means melting point)

D. Pharmacological Example

A) Measurement of Inhibition of DGAT1 Activity by the Present Compounds

The inhibiting activity of the present compounds on DGAT1 activity was screened in a single well procedure assay using DGAT1 comprising membrane preparations and DGAT1 substrate comprising micelles and determining formed radio-active triacylglycerol coming in close proximity of a flashplate surface by radio luminescence.

Said assay is described in full detail in WO2006/067071, the content of which is incorporated herein by reference.

By DGAT1 activity is meant the transfer of coenzyme A activated fatty acids to the 3-position of 1,2-diacylglycerols, thus forming a triglyceride molecule, by enzyme DGAT1.

Step 1 of the Assay: Expression of DGAT1 human DGAT1 (NM012079.2) was cloned into the pFast-Bac vector, containing translation start, a FLAG-tag at the N-terminus as described in literature and a viral Kozak sequence (AAX) preceding the ATG to improve expression in insect cells. Expression was done as described in literature (Cases, S., Smith, S. J., Zheng, Y., Myers H. M., Lear, S. R., Sande, E., Novak, S., Collins, C., Welch, C. B., Lusis, A. J., Erickson, S. K. and Farese, R. V. (1998) Proc. Natl. Acad. Sci. USA 95, 13018-13023.) using SF9 cells.

Step 2 of the Assay: Preparation of DGAT1 Membranes 72 h transfected SF9 cells were collected by centrifugation (13000 rpm-15 min-4° C.) and lysed in 2×500 ml lysisbuffer (0.1M Sucrose, 50 mM KCl, 40 mM KH$_2$PO$_4$, 30 mM EDTA pH 7.2. Cells were homogenized by cell disruptor. After centrifugation 1380 rpm-15 min-4° C. (SN discarded), pellet was resuspended in 500 ml lysisbuffer and total cell membranes collected by ultracentrifugation at 34000 rpm (100 000 g) for 60 min (4° C.). The collected membranes were resuspended in lysis buffer, divided in aliquots and stored with 10% glycerol at −80° C. until use.

Step 3 of the Assay: Preparation of DGAT Substrate Comprising Micelles

Materials a) 1,2-dioleoyl-sn-glycerol, 10 mg/ml (1,2-diacylglycerol (DAG))

Dissolve in acetonitrile; evaporate the acetonitrile solution under nitrogen and reconstitute in chloroform at a final concentration of 10 mg/ml.

b) L-α-phosphatidylcholine, 1 mg/ml (phosphatidylcholine (PC))

Dissolve in chloroform at a final concentration of 1 mg/ml and store at 4° C.

c) L-α-phosphatidyl-L-serine, 1 mg/ml (phophatidylserine (PS))

Dissolve in chloroform at a final concentration of 1 mg/ml and store at 4° C.

Method

Add 1 ml dioleoyl-sn-glycerol (10 mg/ml) to 10 ml of L-α-phosphatidylcholine (1 mg/ml) and 10 ml of L-α-phosphatidyl-L-serine (1 mg/ml) in a thick glass recipient. Evaporate under nitrogen and put on ice for 15 minutes. Reconstitute in 10 ml Tris/HCl (10 mM, pH 7.4) by sonication on ice. The sonification process consists of sonification cycles of 10 seconds in the sonification bath followed by 10 seconds cool down on ice and repeating this sonification cycle till a homogeneous solution is obtained (takes about 15 minutes). The thus obtained micelles are stored at −20° C. till later use and contain DAG at a final concentration of 1.61 mM.

Step 4 of the Assay: DGAT FlashPlate™ Assay

Materials a) Assaybuffer
   50 mM Tris-HCl (pH 7.4), 150 mM $MgCl_2$, 1 mM EDTA, 0.2% BSA.
b) N-ethylmaleimide, 5M
   Dissolve 5 g into a final volume of 8 ml DMSO 100% and store at −20° C. in aliquots till later use.
c) Substrate mix (for 1 384 well plate=3840 μl)
   612 μl micelles stock (51 μM final)
   16.6 μl oleoylCoA 9.7 mM
   23 μl [$^3$H]-oleoylCoA (49 Ci/mmol, 500 μCi/ml) 3188.4 μl Tris pH 7.4, 10 mM
d) Enzyme mix (for 1 384 well plate=3520 μl) (5 μg/ml)
   Add 11.73 μl of DGAT membrane stock (1500 μg/ml stock) to 3508 μl assay buffer.
e) Stop mix (for 1 384 well plate=7.68 ml) (250 mM)
   Add 384 μl of N-ethylmaleimide (5M) to 3.456 ml DMSO 100%, and further dilute 3.84 ml of said solution with 3.84 ml DMSO 10%.

Method

DGAT activity in membrane preparations was assayed in 50 mM Tris-HCl (pH 7.4), 150 mM $MgCl_2$, 1 mM EDTA and 0.2% BSA, containing 50 μM DAG, 32 m/ml PC/PS and 8.4 μM [$^3$H]-oleoylCoA (at a specific activity of 30 nCi/well) in a final volume of 50 μl in 384-well format using the red shifted Basic Image FlashPlate™ (Perkin Elmer Cat. No. SMP400).

In detail, 10 μl enzyme mix and 10 μl substrate mix were added to 30 μl of assay buffer, optionally in the presence of 1 μl DMSO (blank and controls) or 1 μl of the compound to be tested. This reaction mixture was incubated for 120 minutes at 37° C. and the enzymatic reaction stopped by adding 20 μl of the stop mix. The plates were sealed and the vesicles allowed to settle overnight at room temperature. Plates were centrifuged for 5 minutes at 1500 rpm and measured in Leadseeker.

Experiments with different concentrations of the test compound were performed and curves were calculated and drawn based on % $CTRL_{min}$ (% of normalized control). % $CTRL_{min}$ was calculated according to equation 1, $$\% \ CTRL_{min} = (sample - LC)/(HC - LC) \quad \text{Equation 1}$$

where HC (high control) refers to the median of radio luminescence value measured in the wells with enzyme and substrate but without test compound, LC (low control) refers to median background radioluminescence value measured in the wells with substrate without enzyme and without test compound, and sample refers to the radio luminescence value measured in the wells with substrate, enzyme and test compound at a particular concentration.

The calculated % $CTRL_{min}$ values form a sigmoidal dose response descending curve and from this curve $pIC_{50}$ values were calculated ($-logIC_{50}$ where $IC_{50}$ represents the concentration at which the test compound gives 50% inhibition of DGAT1 activity). Table 2 shows the $pIC_{50}$ values for the compounds of formula (I).

In order to determine selectivity of the present compounds for DGAT1 compared to DGAT2, the inhibiting activity of the compounds on DGAT2 was also determined in the above assay, slightly modified to obtain optimal assay conditions for DGAT2. The tested compounds did not show inhibiting activity for DGAT2 (Human DGAT2 (NM032564) was cloned and expressed as described in J. Biolog. Chem. 276(42), pp 38870-38876 (2001)).

TABLE 2

| $pIC_{50}$ values ($IC_{50}$ values expressed in M) | |
|---|---|
| Co. No. | $pIC_{50}$ (mean) |
| 1 | 8.04 |
| 2 | 5.74 |
| 3 | 7.47 |
| 4 | 7.44 |
| 5 | 5.87 |
| 6 | 8.62 |
| 7 | 8.28 |
| 8 | 8.23 |
| 9 | 8.20 |
| 10 | 8.17 |
| 11 | 8.16 |
| 12 | 7.84 |
| 13 | 7.58 |
| 14 | 7.24 |
| 15 | 7.20 |
| 16 | 6.79 |
| 17 | 6.64 |
| 18 | 6.10 |
| 19 | 5.54 |

B) In Vivo Study for Effect of Test Compound on GLP-1 Plasma Levels

Elevation of GLP-1 plasma levels by a DGAT inhibitor can be studied as follows:

Dogs are deprived from food for a period of 22 hours. At time 0, animals are given a liquid meal, containing 18% fat (w/w), by gavage with a stomach tube. The test compound is given orally together with the meal. Afterwards, a postprandial plasma profile is determined for GLP-1. Therefore, blood is collected at predetermined time intervals in ice-cooled Vacutainers EDTA-plasma tubes and GLP-1 levels are measured in the samples taken at 0 hour (just before the meal) and at 0.5, 1, 2, 4, 6, 8 and 24 hours after dosing. Six dogs (3 males and 3 females) are included per dosage group and the plasma GLP-1 profile is compared with their own GLP-1 profile previously determined in the same conditions but without administration of the test compound.

GLP-1 determinations in plasma are performed with a Glucagon-like peptide-1 (active) ELISA kit 96-well plate of LINCO Research.

E. Composition Examples

"Active ingredient" (a.i.) as used throughout these examples relates to a compound of formula (I), including any stereochemically isomeric form thereof, a N-oxide thereof, a pharmaceutically acceptable salt thereof or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

The invention claimed is:

1. A compound having the following formula

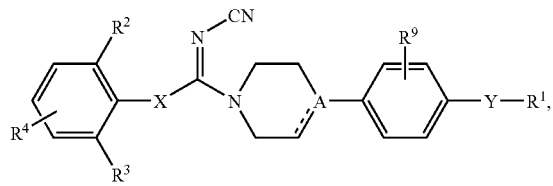

(I)

including any stereochemically isomeric form thereof, wherein

A represents N;

X represents O or $NR^x$;

the dotted line represents an optional bond in case A represents a carbon atom;

Y represents a direct bond; $-NR^x-C(=O)-$; $-C(=O)-NR^x-$; $-NR^x-C(=O)-Z-$; $-NR^x-C(=O)-Z-NR^y-$; $-NR^x-C(=O)-Z-NR^y-C(=O)-$; $-NR^x-C(=O)-Z-NR^y-C(=O)-O-$; $-NR^x-C(=O)-Z-O-$; $-NR^x-C(=O)-Z-O-C(=O)-$; $-NR^x-C(=O)-Z-C(=O)-$; $-NR^x-C(=O)-Z-C(=O)-O-$; $-NR^x-C(=O)-O-Z-C(=O)-$; $-NR^x-C(=O)-O-Z-C(=O)-$; $-NR^x-C(=O)-O-Z-O-C(=O)-$; $-NR^x-C(=O)-Z-C(=O)-NR^y-$; $-NR^x-C(=O)-Z-NR^y-C(=O)-NR^y-$; $-C(=O)-Z-$; $-C(=O)-Z-O-$; $-C(=O)-NR^x-Z-$; $-C(=O)-NR^x-Z-O-$; $-C(=O)-NR^x-Z-O-C(=O)-$; $-C(=O)-NR^x-Z-O-C(=O)-$; $-C(=O)-NR^x-O-Z-$; $-C(=O)-NR^x-Z-NR^y-$; $-C(=O)-NR^x-Z-NR^y-C(=O)-$; or $-C(=O)-NR^x-Z-NR^y-C(=O)-O-$;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$alkenyl; or $-S(=O)_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; aryl$^1$; aryl$^1C_{1-6}$alkyl; Het$^1$; or Het$^1C_{1-6}$alkyl; provided that when Y represents $-NR^x-C(=O)-Z-$; $-NR^x-C(=O)-Z-NR^y$; $-NR^x-C(=O)-Z-C(=O)-NR^y-$; $-C(=O)-Z-$; $-NR^x-C(=O)-Z-NR^y-C(=O)-NR^y-$; $-C(=O)-NR^x-Z-$; $-C(=O)-NR^x-O-Z-$; or $-C(=O)-NR^x-Z-NR^y-$; then $R^1$ may also represent hydrogen;

$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; or $-S(=O)_p-C_{1-4}$alkyl;

$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; $C_{1-4}$alkylcarbonylamino; $-S(=O)_p-C_{1-4}$alkyl; $R^6R^5N-C(=O)-$; $R^6R^5N-C_{1-6}$alkyl; $C_{3-6}$cycloalkyl; aryl; aryloxy; aryl$C_{1-4}$alkyl; aryl-$C(=O)-C_{1-4}$alkyl; aryl-$C(=O)-$; Het; Het$C_{1-4}$alkyl; Het-$C(=O)-C_{1-4}$alkyl; Het-$C(=O)-$; or Het-O-;

$R^5$ represents hydrogen; $C_{1-4}$alkyl optionally substituted with hydroxyl or $C_{1-4}$alkyloxy; $R^8R^7N-C_{1-4}$alkyl; $C_{1-4}$alkyloxy; Het; aryl; or $R^8R^7N-C(=O)-C_{1-4}$alkyl;

$R^6$ represents hydrogen or $C_{1-4}$alkyl;

$R^7$ represents hydrogen; $C_{1-4}$alkyl; or $C_{1-4}$alkylcarbonyl;

$R^8$ represents hydrogen or $C_{1-4}$alkyl; or $R^7$ and $R^8$ may be taken together with the nitrogen to which they are attached to form a saturated monocyclic 5, 6 or 7-membered heterocycle which may further contain one or more heteroatoms each independently selected from the group consisting of O, S, $S(=O)_p$ and N; and which heterocycle may optionally be substituted with $C_{1-4}$alkyl;

$R^9$ represents hydrogen; halo; $C_{1-4}$alkyl; or $C_{1-4}$alkyl substituted with hydroxyl;

aryl represents phenyl or phenyl substituted with at least one substituent, each substituent independently being selected from the group consisting of hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; and $-S(=O)_p-C_{1-4}$alkyl;

aryl¹ represents phenyl, naphthalenyl or fluorenyl; each of said phenyl, naphthalenyl or fluorenyl optionally substituted with at least one substituent, each substituent independently being selected from the group consisting of hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono- or di($C_{1-6}$alkyl)amino; $R^6R^5N$—$C_{1-6}$alkyl; $C_{3-6}$cycloalkyl-$NR^x$—; aryl-$NR^x$—; Het-$NR^x$—; $C_{3-6}$cycloalkyl-$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; and Het-O—;

Het represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi-or tricyclic heterocycle optionally being substituted with at least one substituent, each substituent independently being selected from the group consisting of hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

Het¹ represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; amino; mono- or di($C_{1-6}$alkyl)amino; $R^6R^5N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; and Het-O—;

p represents 1 or 2;

a N-oxide thereof, a pharmaceutically acceptable salt thereof or a solvate thereof.

2. The compound as claimed in claim 1 having the following formula

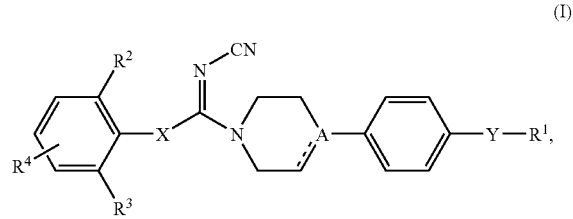

(I)

including any stereochemically isomeric form thereof, wherein

A represents N;

X represents O or $NR^x$;

the dotted line represents an optional bond in case A represents a carbon atom;

Y represents a direct bond; —$NR^x$—C(=O)—; —C(=O)—$NR^x$—; —$NR^x$—C(=O)—Z—; —$NR^x$—C(=O)—Z—$NR^y$—; —$NR^x$—C(=O)—Z—$NR^y$—C(=O)—; —$NR^x$—C(=O)—Z—$NR^y$—C(=O)—O—; —$NR^x$—C(=O)—Z—O—; —$NR^x$—C(=O)—Z—O—C(=O)—; —$NR^x$—C(=O)—Z—C(=O)—; —$NR^x$—C(=O)—Z—C(=O)—O—; —$NR^x$—C(=O)—O—Z—C(=O)—; —$NR^x$—C(=O)—O—Z—C(=O)—O—; —$NR^x$—C(=O)—O—Z—O—C(=O)—; —$NR^x$—C(=O)—Z—C(=O)—$NR^y$—; —$NR^x$—C(=O)—Z—$NR^y$—C(=O)—$NR^y$—; —C(=O)—Z—; —C(=O)—Z—O—; —C(=O)—$NR^x$—Z—; —C(=O)—$NR^x$—Z—O—; —C(=O)—$NR^x$—Z—C(=O)—O—; —C(=O)—$NR^x$—Z—O—C(=O)—; —C(=O)—$NR^x$—O—Z—; —C(=O)—$NR^x$—Z—$NR^y$—; —C(=O)—$NR^x$—Z—$NR^y$—C(=O)—; or —C(=O)—$NR^x$—Z—$NR^y$—C(=O)—O—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$alkenyl; or —S(=O)$_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; aryl¹; aryl¹$C_{1-6}$alkyl; Het¹; or Het¹$C_{1-6}$alkyl; provided that when Y represents —$NR^x$—C(=O)—Z—; —$NR^x$—C(=O)—Z—$NR^y$; —$NR^x$—C(=O)—Z—C(=O)—$NR^y$—; —C(=O)—Z—; —$NR^x$—C(=O)—Z—$NR^y$—C(=O)—$NR^y$—; —C(=O)—$NR^x$—Z—; —C(=O)—$NR^x$—O—Z—; or —C(=O)—$NR^x$—Z—$NR^y$—; then $R^1$ may also represent hydrogen;

$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; or —S($=$O)$_p$—$C_{1-4}$alkyl;

$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S($=$O)$_p$—$C_{1-4}$alkyl; $R^6R^5N$—C($=$O)—; $R^6R^5N$—$C_{1-6}$alkyl; $C_{3-6}$cycloalkyl; aryl; aryloxy; aryl$C_{1-4}$alkyl; aryl-C($=$O)—; Het; Het$C_{1-4}$alkyl; Het-C($=$O)—; or Het-O—;

$R^5$ represents hydrogen; $C_{1-4}$alkyl optionally substituted with hydroxyl or $C_{1-4}$alkyloxy; $R^8R^7N$—$C_{1-4}$alkyl; $C_{1-4}$alkyloxy; Het; aryl; or $R^8R^7N$—C($=$O)—$C_{1-4}$alkyl;

$R^6$ represents hydrogen or $C_{1-4}$alkyl;

$R^7$ represents hydrogen; $C_{1-4}$alkyl; or $C_{1-4}$alkylcarbonyl;

$R^8$ represents hydrogen or $C_{1-4}$alkyl; or $R^7$ and $R^8$ may be taken together with the nitrogen to which they are attached to form a saturated monocyclic 5, 6 or 7-membered heterocycle which may further contain one or more heteroatoms selected from of O, S, S($=$O)$_p$ or N; and which heterocycle may optionally be substituted with $C_{1-4}$alkyl;

aryl represents phenyl or phenyl substituted with at least one substituent, each substituent independently being selected from the group consisting of hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S($=$O)$_p$—$C_{1-4}$alkyl;

aryl$^1$ represents phenyl, naphthalenyl or fluorenyl; each of said phenyl, naphthalenyl or fluorenyl optionally substituted with at least one substituent, each substituent independently being selected from the group consisting of hydroxyl; oxo; carboxyl; halo; $C_{1-6}$alkyl optionally substituted with aryl-C($=$O)—; hydroxy$C_{1-6}$alkyl optionally substituted with aryl or aryl-C($=$O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het $C_{1-4}$alkyl-$NR^x$—; —S($=$O)$_p$—$C_{1-4}$alkyl; $C_{3-6}$cycloalkyl; $C_{3-6}$cycloalkyl$C_{1-4}$alkyl; $C_{3-6}$cycloalkyl-C($=$O)—; aryl; aryloxy; aryl$C_{1-4}$alkyl; aryl-C($=$O)—; Het; Het$C_{1-4}$alkyl; Het-C($=$O)—; and Het-O—;

Het represents a monocyclic non-aromatic or aromatic heterocycle containing at least one heteroatom selected from the group consisting of O, S, S($=$O)$_p$ and N; or a bicyclic or tricyclic non-aromatic or aromatic heterocycle containing at least one heteroatom selected from the group consisting of O, S, S($=$O)$_p$ and N; said monocyclic heterocycle or said bi- or tricyclic heterocycle optionally being substituted with at least one substituent, each substituent independently being selected the group consisting of from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono-or di($C_{1-4}$alkyl)amino; and —S($=$O)$_p$—$C_{1-4}$alkyl;

Het$^1$ represents a monocyclic non-aromatic or aromatic heterocycle containing at least one heteroatom selected from the group consisting of O, S, S($=$O)$_p$ and N; or a bicyclic or tricyclic non-aromatic or aromatic heterocycle containing at least one heteroatom selected from the group consisting of O, S, S($=$O)$_p$ and N; said monocyclic heterocycle or said bi-or tricyclic heterocycle optionally being substituted with at least one substituent, each substituent independently being selected from the group consisting of hydroxyl; oxo; carboxyl; halo; $C_{1-6}$alkyl optionally substituted with aryl-C($=$O)—; hydroxy$C_{1-6}$alkyl optionally substituted with aryl or aryl-C($=$O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S($=$O)$_p$—$C_{1-4}$alkyl; $C_{3-6}$cycloalkyl; $C_{3-6}$cycloalkyl$C_{1-4}$alkyl; $C_{3-6}$cycloalkyl-C($=$O)—; aryl; aryloxy; aryl$C_{1-4}$alkyl; aryl-C($=$O)—; Het; Het$C_{1-4}$alkyl; Het-C($=$O)—; and Het-O—;

p represents 1 or 2;

a N-oxide thereof, or a pharmaceutically acceptable salt thereof.

3. The compound as claimed in claim 1 wherein X represents NH.

4. The compound as claimed in claim 1 wherein Y represents —$NR^x$—C($=$O)—; —$NR^x$—C($=$O)—Z—, —$NR^x$—C($=$O)—Z—$NR^y$—; or —$NR^x$—C($=$O)—Z—O—C($=$O)—.

5. The compound as claimed in claim 4 wherein Y represents —$NR^x$—C($=$O)— or —$NR^x$—C($=$O)—Z—.

6. The compound as claimed in claim 1 wherein $R^2$ and $R^3$ each independently represent hydrogen, halo or $C_{1-6}$alkyl.

7. The compound as claimed in claim 1 wherein $R^4$ represents hydrogen; carboxyl; $C_{1-6}$alkyloxycarbonyl; Het-C($=$O)— or Het$C_{1-4}$alkyl.

8. The compound as claimed in claim 1 wherein $R^1$ represents aryl$^1$ or Het$^1$.

9. The compound as claimed in claim 1 wherein

X represents NH or O; $R^2$ represents hydrogen, halo or $C_{1-6}$alkyl; $R^3$ represents hydrogen, halo or $C_{1-6}$alkyl; $R^4$ represents hydrogen; carboxyl; $C_{1-6}$alkyloxycarbonyl; Het-C($=$O)— or Het$C_{1-4}$alkyl;

Y represents —$NR^x$—C($=$O)—; —$NR^x$—C($=$O)—Z—, —$NR^x$—C($=$O)—Z—$NR^y$—; or —$NR^x$—C($=$O)—Z—O—C($=$O)—;

Z represents $C_{1-6}$alkanediyl;

$R^1$ represents hydrogen; $C_{1-12}$alkyl; aryl$^1$ or Het$^1$; $R^x$ represents hydrogen; $R^y$ represents hydrogen; $R^9$ represents hydrogen; $R^4$ is placed in para position.

10. The compound as claimed in claim 1 wherein the compound is selected from

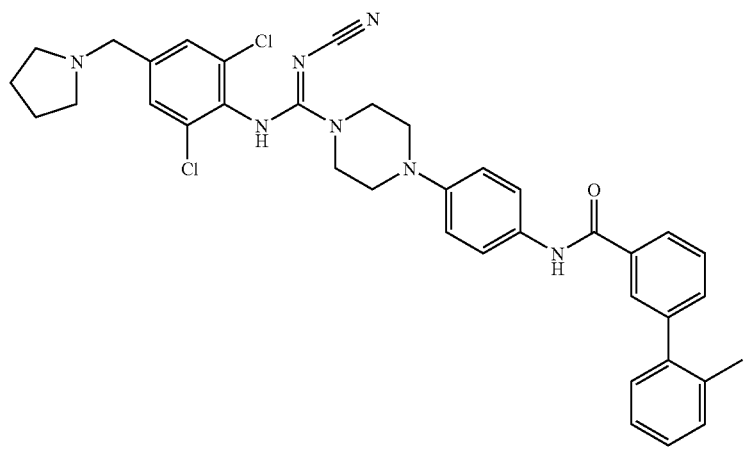

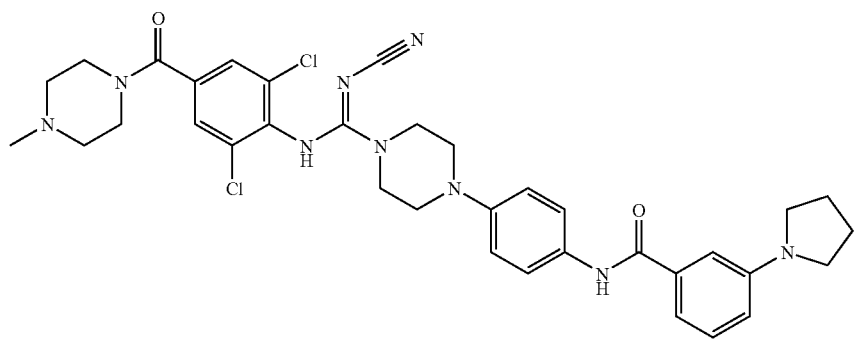

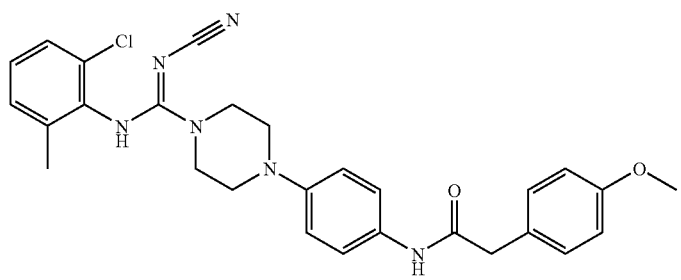

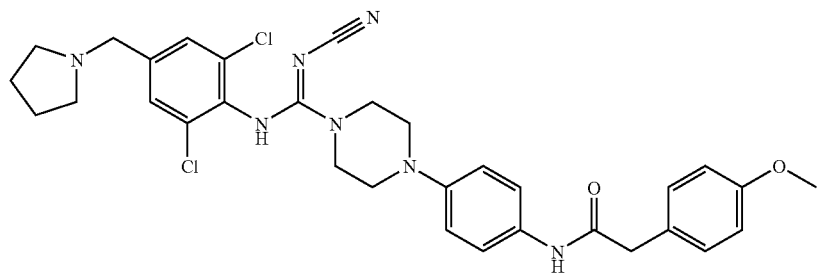

a N-oxide thereof, a pharmaceutically acceptable salt thereof.

11. A pharmaceutical composition comprising a pharmaceutically acceptable carrier, and a compound as claimed in claim 1.

12. A process of preparing a compound as defined in claim 1 comprising a) reacting an intermediate of formula (II) with cyanamide in the presence of a suitable solvent, to produce the compound of formula (I-a)

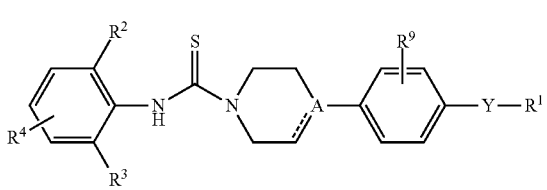

(II)

-continued (I-a)

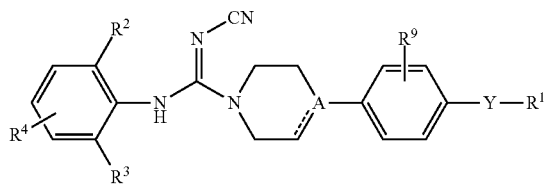

b) reacting an intermediate of formula (III) wherein $W_1$ represents a suitable leaving group, with an intermediate of formula (IV) in the presence of a suitable solvent, to produce the compound of formula (I-b):

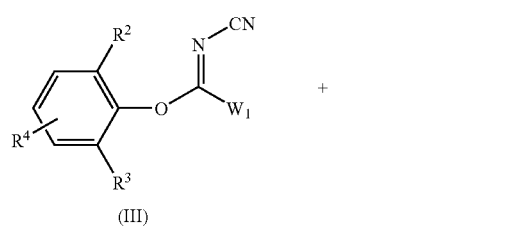

(III)

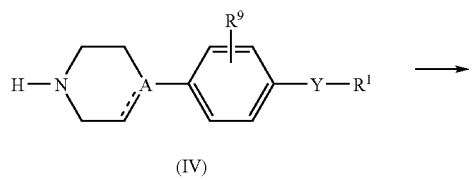

(IV)

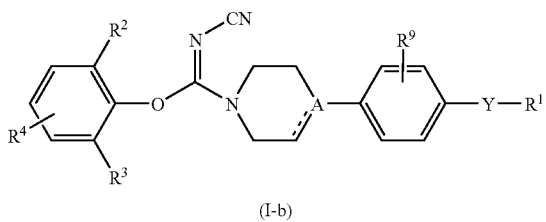

(I-b)

c) reacting a compound of formula (I-b) with an intermediate of formula (V) in the presence of a suitable reducing agent and a suitable solvent, to produce the compound of formula (I-a):

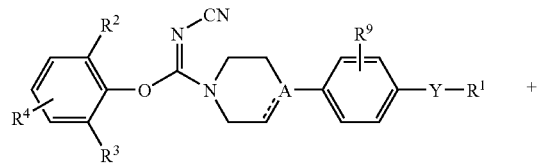

(I-b)

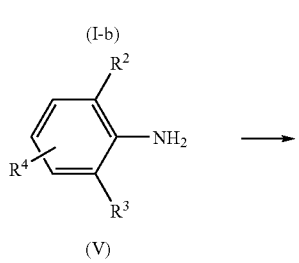

(V)

-continued (I-a)

d) reacting an intermediate of formula (XIX) with an intermediate of formula (XIII) in the presence of a suitable dehydrating (coupling) agent in the presence of a suitable solvent and optionally in the presence of a suitable base, to produce the compound of formula (I-c):

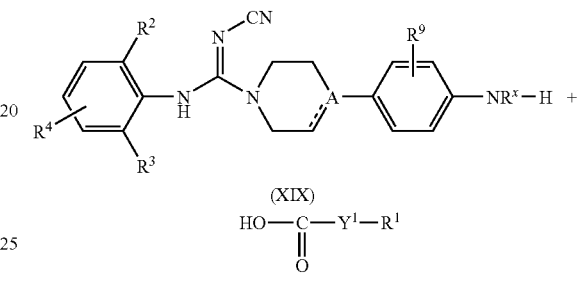

(XIX)

$$HO-\underset{O}{\underset{\|}{C}}-Y^1-R^1$$

(XIII)

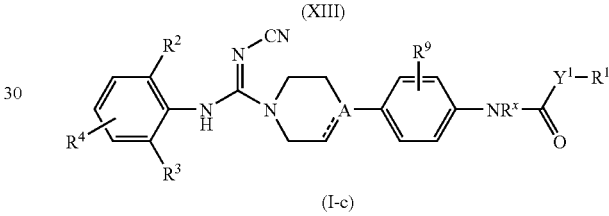

(I-c)

with $Y^1$ representing the remainder of the linker Y including a direct bond;

e) reacting an intermediate of formula (XIX) with an intermediate of formula (XX) wherein $W_1$ represents a suitable leaving group, in the presence of a suitable base and a suitable solvent, to produce the compound of formula (I-c):

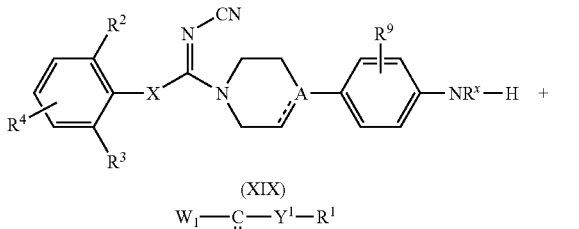

(XIX)

$$W_1-\underset{O}{\underset{\|}{C}}-Y^1-R^1$$

(XX)

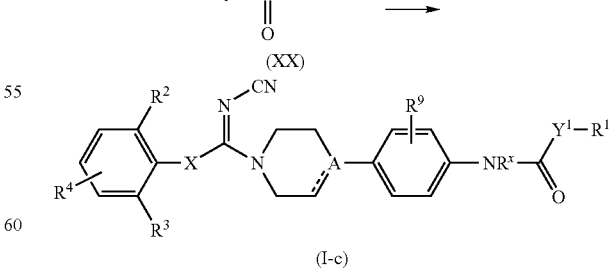

(I-c)

with $Y^1$ is a direct bond; —Z—; -z-NRY—; —Z—NRY—C(=O)—; —Z—NRY—C(=O)—O—; —Z—O; —Z—O—C(=O)—; —Z—C(=O)—; —Z—C(=O)—O—; —O—Z—C(=O)—; —O—Z—C (=O)—O—; —O—Z—O—C(=O)—; —Z—C(=O)—NRY—; or —Z—NRY—C(=O)—NRY—;

f) reacting an intermediate of formula (XXI) wherein W₂ represents a suitable leaving group, with an intermediate of formula (XXII) in the presence of a suitable base and a suitable solvent, to produce the compound of formula (I-d):

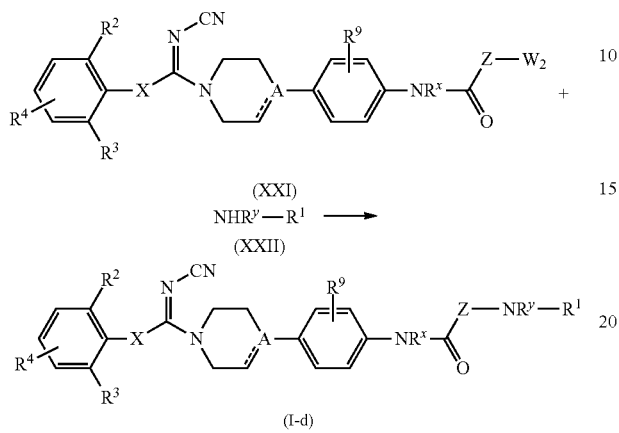

(XXI)

NHR^y—R¹

(XXII)

(I-d)

g) reacting an intermediate of formula (XXI) with an intermediate of formula (XXIII) in the presence of a suitable base and a suitable solvent, to produce the compound of formula (I-e)

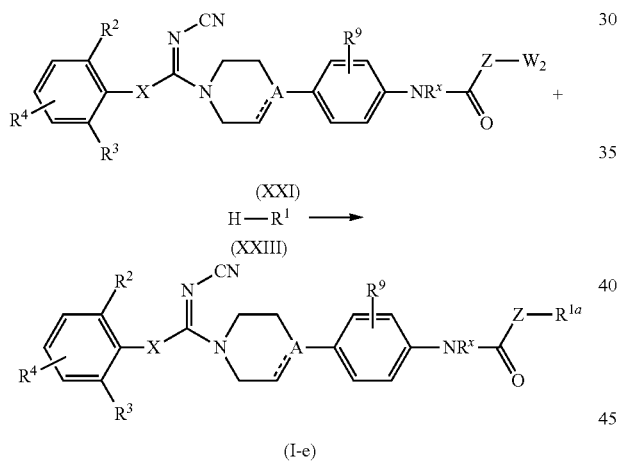

(XXI)

H—R¹

(XXIII)

(I-e)

with R¹ representing an optionally substituted monocyclic saturated heterocycle linked with a nitrogen atom to Z, said R¹ being represented by R^{1a};

or h) deprotecting an intermediate of formula (XXIV) wherein P represents a suitable protecting group, in the presence of a suitable acid and a suitable solvent, to produce the compound of fromula (I-f):

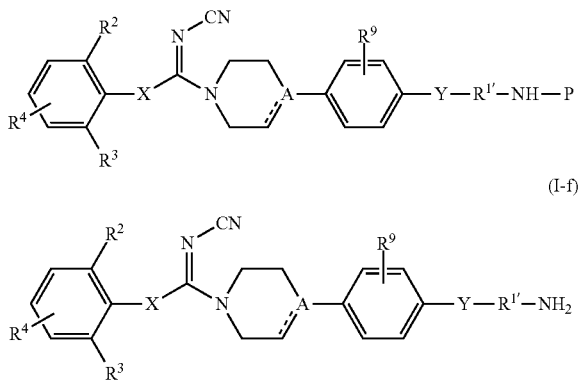

with R¹ being substituted with NH₂, said R¹ being represented by R^{1'}—NH₂;

and further, optionally converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; or, optionally preparing stereochemically isomeric forms, quaternary amines, solvates or N-oxide forms thereof.

13. The pharmaceutical composition as in claim 11, further comprising an agonist of peroxisome proliferator-activator receptor.

* * * * *